US012760262B2

(12) United States Patent
Natarajan et al.

(10) Patent No.: US 12,760,262 B2
(45) Date of Patent: Oct. 13, 2026

(54) IN-PROCESS VERIFICATION OF CALIBRATION STATUS OF pH PROBES

(71) Applicant: AMGEN INC., Thousand Oaks, CA (US)

(72) Inventors: Venkatesh Natarajan, Thousand Oaks, CA (US); Marco DeLiso, Thousand Oaks, CA (US); Jeremy Aaron Bezaire, North Reading, MA (US); Andrew Cavigli, Boston, MA (US); Jeremy S. Conner, Newbury Park, CA (US); Jon Hunter, Cambridge, MA (US); Sidney Pehrson, Belmont, MA (US); Sarah Whetstone, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 730 days.

(21) Appl. No.: 18/035,316

(22) PCT Filed: Nov. 9, 2021

(86) PCT No.: PCT/US2021/058508
§ 371 (c)(1),
(2) Date: May 4, 2023

(87) PCT Pub. No.: WO2022/099162
PCT Pub. Date: May 12, 2022

(65) Prior Publication Data

US 2023/0416667 A1 Dec. 28, 2023

Related U.S. Application Data

(60) Provisional application No. 63/168,608, filed on Mar. 31, 2021, provisional application No. 63/111,502, filed on Nov. 9, 2020.

(51) Int. Cl.
*C12M 1/12* (2006.01)
*C12M 1/00* (2006.01)
(Continued)

(52) U.S. Cl.
CPC ............ *C12M 37/00* (2013.01); *C12M 37/06* (2013.01); *C12M 41/26* (2013.01); *C12M 47/10* (2013.01); *C12N 7/00* (2013.01)

(58) Field of Classification Search
CPC ...... C12M 37/00; C12M 37/06; C12M 41/26; C12M 47/10; C12M 47/16; C12N 7/00; C07K 1/36; C07K 1/22
(Continued)

(56) References Cited

U.S. PATENT DOCUMENTS

| | | | |
|---|---|---|---|
| 11,371,006 | B2 | 6/2022 | Eisenkraetzer et al. |
| 2012/0052560 | A1 | 3/2012 | Knight et al. |

(Continued)

FOREIGN PATENT DOCUMENTS

| | | | |
|---|---|---|---|
| CN | 103946364 | A | 7/2014 |
| JP | 2018534560 | A | 11/2018 |

(Continued)

OTHER PUBLICATIONS

Kateja et al. Biochemical Engineering Journal, vol. 167,107885, pp. 1-9, Dec. 19, 2020.*

(Continued)

*Primary Examiner* — Maureen Wallenhorst
(74) *Attorney, Agent, or Firm* — MARSHALL, GERSTEIN & BORUN LLP

(57) ABSTRACT

Automated systems and methods for low-pH viral inactivation include adding an elution pool to a first vessel with an acid. Once first vessel pH probes measure sufficiently low pH, the pool is transferred to a second vessel, where the pH is checked again, and the pool is held for a time sufficient to reduce virus concentration to a safe level, and neutralized, filtered, and transferred to a third vessel. Meanwhile, the first vessel is filled with a known-pH buffer, which is checked against readings from first vessel pH probes to determine whether recalibration is needed. After the pool is transferred to the third vessel, the second vessel is filled with a known-pH buffer, which is checked against readings from second vessel pH probes to determine whether recalibration is needed. The process repeats when the known-pH buffer is dumped and a new elution pool is added to the first vessel.

20 Claims, 7 Drawing Sheets

(51) Int. Cl.
*C12M 1/34* (2006.01)
*C12N 7/00* (2006.01)

(58) Field of Classification Search
USPC ............ 422/63, 70, 559; 436/43, 50, 55, 63, 436/161, 163; 435/5
See application file for complete search history.

(56) References Cited

U.S. PATENT DOCUMENTS

| | | | | |
|---|---|---|---|---|
| 2012/0264920 | A1* | 10/2012 | Wang | B01D 15/125 530/416 |
| 2015/0064769 | A1* | 3/2015 | Xenopoulos | C12N 7/00 435/238 |
| 2017/0037381 | A1* | 2/2017 | Coffman | C12N 7/00 |
| 2018/0216059 | A1 | 8/2018 | Eisenkraetzer et al. | |
| 2022/0090001 | A1* | 3/2022 | Bartake | C12M 37/00 |
| 2022/0235311 | A1* | 7/2022 | Vandiver | C12M 37/00 |
| 2022/0356454 | A1* | 11/2022 | Fiadeiro | C07K 16/00 |

FOREIGN PATENT DOCUMENTS

| | | | |
|---|---|---|---|
| RU | 2234703 | C1 | 8/2004 |
| TW | 201717974 | A | 6/2017 |
| TW | 202003832 | A | 1/2020 |
| WO | WO-2012171030 | A3 | 5/2013 |
| WO | WO-2014004103 | A1 | 1/2014 |
| WO | WO-2017156355 | A1 | 9/2017 |
| WO | WO-2020/076681 | A1 | 4/2020 |
| WO | WO-2020/152509 | A1 | 7/2020 |
| WO | WO-2020/168315 | A1 | 8/2020 |

OTHER PUBLICATIONS

Gillespie et al. Biotechnology Journal, vol. 14, 1700718, pp. 1-9, 2019.*
International Application No. PCT/US2021/058508, International Search Report and Written Opinion, mailed Mar. 1, 2022.

* cited by examiner

Two Vessel Design To Prevent The Hanging Drop Issue

IN-PROCESS VERIFICATION OF CALIBRATION STATUS OF pH PROBES

CROSS-REFERENCE TO RELATED APPLICATIONS

This application is the U.S. National Stage of International Application No. PCT/US2021/058508, filed Nov. 9, 2021, which claims priority to Provisional Application No. 63/111,502, entitled "IN-PROCESS VERIFICATION OF CALIBRATION STATUS OF PH PROBES", filed Nov. 9, 2020; and Provisional Application No. 63/168,608, entitled "IN-PROCESS VERIFICATION OF CALIBRATION STATUS OF PH PROBES", filed Mar. 31, 2021; the disclosures of each of which are incorporated herein by reference in their entirety.

FIELD OF THE DISCLOSURE

The present disclosure generally relates to viral inactivation and, more particularly, to techniques for automated viral inactivation, including automated cycles of pH adjustment.

BACKGROUND

The background description provided herein is for the purpose of generally presenting the context of the disclosure. Work of the presently named inventors, to the extent it is described in the background section, as well as aspects of the description that may not otherwise qualify as prior art at the time of filing, are neither expressly nor impliedly admitted as prior art against the present disclosure.

Manufacturing therapeutic recombinant biologic products using cell culture processes carries an inherent risk of transmitting viral contaminants. Such contaminants can arise from a variety of sources, including starting materials, the use of reagents of animal origin, and/or through contamination of the manufacturing system due to failures in the GMP process. As such, regulatory authorities recommend that biomanufacturing processes have dedicated viral inactivation and virus removal steps and request manufacturers validate the removal and inactivation of viruses to ensure the safety of the recombinant biologic products. The viral inactivation step focuses on enveloped viruses (e.g., retroviruses), and the virus filtration step removes those viruses that are not impacted by the inactivation methods (non-enveloped viruses). Some commonly-used methods of inactivating enveloped viruses include breaching the envelope by heat, use of solvents and/or detergents, and/or low pH treatment. When inactivating a virus using an inactivating agent, such as a detergent, further purification is required to remove the detergent. Advantageously, low pH viral inactivation does not require further purification to remove the inactivating agent.

Viral inactivation can be performed throughout a downstream purification process. Guiding factors that help determine the location of a viral inactivation unit operation include the impact of the viral inactivation step on the succeeding unit operations, and, if an inactivating agent such as a detergent or solvent is used, how well can the agent can be cleared in the subsequent downstream steps, as well as whether the conditions of a particular unit operation dovetail with the viral inactivation step. For example, a viral inactivation unit operation is typically performed after the first step in a downstream process following harvest of the cell culture fluid from the bioreactor. Typically, this is an affinity chromatography step that removes nearly all of the impurities from the harvested fluid. Protein A is a commonly used affinity chromatography method for proteins that have an Fc region, such as antibodies. Since elution from the Protein A chromatography column is typically performed at a lower pH, a low pH viral inactivation step dovetails well because the elution fluid is already at a reduced pH. The acidified elution fluid is held for an amount of time that has been determined to inactivate the virus concentration by the required number of logs. This step is followed by neutralization, typically to pH 5 or above, because the recombinantly expressed proteins can be damaged if left at a reduced pH for too long, and the higher pH is typically needed for the following purification steps.

The current industry standard for viral inactivation in the downstream bioprocess is to titrate the eluate pool manually with a pH probe. With the advancement of continuous manufacturing, the frequency of running this process has increased from once per culture run, to at least once per day during the entirety of the production period. This requires a significant increase of labor, and ultimately cost to the process.

Additionally, in a typical viral inactivation unit operation conducted in a holding a vessel, the pH probes are left dry after a viral inactivation cycle is complete, potentially impacting their calibration status. Thus, operational staff must withdraw samples and measure the pH using a benchtop probe to verify the calibration status of the pH probes before a new viral inactivation cycle can begin.

As such, there is a need for methods for reducing the labor and cost required during viral inactivation, and for keeping pH probes wetted and automatically verifying their calibration status for viral inactivation unit operations in manufacturing processes. The invention described herein meets this need by automatic viral inactivation and in-process verification of the calibration of the pH probes.

SUMMARY

In an aspect, an automated system for low pH viral inactivation is provided, the system comprising: a first vessel; a second vessel; a first pH probe associated with the first vessel and configured to measure the pH of contents of the first vessel; a source of a fluid known or suspected to contain at least one enveloped virus to be transferred to the first vessel; an acid pump configured to pump acid into the first vessel after the fluid is transferrred into the first vessel and configured to cease pumping acid into the first vessel responsive to the first pH probe measuring a first pH value that is within a tolerance band of a target pH value for viral inactivation; a transfer pump configured to pump the acidified pool from the first vessel to the second vessel responsive to the first pH probe measuring the first pH value that is below the threshold pH value for viral inactivation, and responsive to the acid pump ceasing to pump acid into the first vessel; a first buffer pump configured to pump a first equilibration buffer, having a first known pH value, into the first vessel responsive to the entire acidified pool being pumped out of the first vessel; and an alert generator configured to: compare a second pH value, measured by the first pH probe after the first equilibration buffer is pumped into the first vessel, to the first known pH value of the first equilibration buffer; determine whether the second pH value measured by the first pH probe is different from the first known pH value of the first equilibration buffer by greater than a threshold pH value; and generate a first alert responsive to the second pH value measured by the first pH probe being different from the first known pH of the first equilibration buffer by greater than the threshold pH value.

In some examples, the system includes a source pump configured to pump the fluid into the first vessel from the source based at least in part on a signal indicating that the first vessel is empty.

Additionally, in some examples, the first buffer pump is configured to pump the first equilibration buffer into the first vessel based at least in part on a signal indicating that the first vessel is empty.

In some examples, the automated system for low pH viral inactivation may further include: a second pH probe associated with the second vessel and configured to measure the pH of contents of the second vessel; a base pump configured to pump base into the second vessel responsive to an elapsed time, from the entire acidified pool being pumped into the second vessel, exceeding a threshold amount of time for reducing a concentration of virus in the acidified pool to a predetermined safe level, and configured to cease pumping base into the second vessel responsive to the second pH probe measuring a first pH value that is within a threshold range of neutral pH values; a discharge pump configured to pump the neutralized viral inactivated pool from the second vessel into a filter for treatment of the neutralized viral inactivated pool; a second buffer pump configured to pump a second equilibration buffer, having a second known pH value, into the second vessel responsive to the entire pool being pumped out of the second vessel; and the alert generator may be further configured to: compare a second pH value, measured by the second pH probe after the first equilibration buffer is pumped into the second vessel, to the second known pH value of the second equilibration buffer; determine whether the second pH value measured by the second pH probe is different from the second known pH value of the second equilibration buffer by greater than the threshold pH value; and generate a second alert responsive to the second pH value measured by the second pH probe being different from the second known pH of the second equilibration buffer by greater than the threshold pH value.

Furthermore, in some examples, the transfer pump is configured to pump the acidified pool from the first vessel to the second vessel based at least in part on a signal indicating that the second vessel is empty.

Additionally, in some examples, the second buffer pump is configured to pump the second equilibration buffer into the second vessel based at least in part on a signal indicating that the second vessel is empty.

Moreover, in some examples, the automated system for low pH viral inactivation may further include a third vessel; and a collection pump configured to pump the filtered pool from the filter to the third vessel.

In some examples, the collection pump is configured to pump the filtered pool from the second vessel to the third vessel based at least in part on a signal indicating that the third vessel is empty.

Additionally, in some examples, the automated system for low pH viral inactivation may further include a first pH probe recalibrator configured to automatically recalibrate the first pH probe responsive to the first alert. Similarly, in some examples, the automated system for low pH viral inactivation may further include a second pH probe recalibrator configured to automatically recalibrate the second pH probe responsive to the second alert.

Furthermore, in some examples, the automated system for low pH viral inactivation may further include one or more additional pH probes associated with the first vessel and configured to measure the pH of contents of the first vessel. Similarly, in some examples, the automated system for low pH viral inactivation may further include one or more additional pH probes associated with the second vessel and configured to measure the pH of contents of the second vessel.

Additionally, in some examples, the automated system for low pH viral inactivation may further include an operator display configured to display one or more of the first alert or the second alert to an operator associated with the system.

Moreover, in some examples, the acid is selected from formic acid, acidic acid, citric acid, and phosphoric acid at concentrations suitable to ensure viral inactivation. Furthermore, in some examples, the threshold pH for viral inactivation is from pH 2 to 4. Additionally, in some examples, the chromatography elution pool is exposed to the acid for less than 30 minutes prior to neutralization. Moreover, in some examples, the base is Tris base at a concentration of 2M. Furthermore, in some examples, the threshold range of neutral pH values is from pH 4.5 to 6. Additionally, in some examples, the low pH viral inactivation is conducted at a temperature of 5 to 25° C.

Furthermore, in some examples, neutralized viral inactivated chromatography elution pool from the second vessel is transferred to a holding vessel. For instance, in some examples, the neutralized viral inactivated chromatography elution pool from the second vessel is transferred to a depth filter. Additionally, in some examples, following depth filtration, the neutralized viral inactivated eluate is transferred to a sterile filter. Moreover, in some examples, the neutralized viral inactivated chromatography elution pool from the second vessel is transferred a first polish chromatography column.

In another aspect, an automated method of low pH viral inactivation is provided, the method comprising: adding a pool to a first vessel; adding acid to the first vessel; measuring, by a first pH probe associated with the first vessel, a first pH value associated with the first vessel; ceasing, based on the first measured pH value associated with the first vessel being within a tolerance band of a target pH value for viral inactivation, the addition of acid to the first vessel; transferring the pool from the first vessel to a second vessel; filling the first vessel with an equilibration buffer having a known pH value; measuring, by the first pH probe, a second pH value associated with the first vessel; comparing the second measured pH value associated with the first vessel to the known pH value of the equilibration buffer; determining whether the second measured pH value associated with the first vessel is different from the known pH value of the equilibration buffer by greater than a threshold pH value; and generating a first alert responsive to the second measured pH value associated with the first vessel being different from the known pH value of the equilibration buffer by greater than the threshold pH value.

In some examples, transferring the pool into the first vessel is based at least in part on receiving a signal indicating that the first vessel is empty.

Additionally, in some examples, filling the first vessel with the equilibration buffer is based at least in part on receiving a signal indicating that the first vessel is empty.

In some examples, the automated method of low pH viral inactivation may further include adding base to the second vessel after an elapsed time after the transfer of the pool to the second vessel exceeds a threshold amount of time for reducing a concentration of virus in the pool to a predetermined safe level; measuring, by a second pH probe associated with the second vessel, a first pH value associated with the second vessel; ceasing, based on the first measured pH value associated with the second vessel being within a threshold range of neutral pH values, the addition of base to the second vessel; transferring the pool from the second vessel to a filter for treatment of the neutralized viral inactivated pool; filling the second vessel with the equilibration buffer having the known pH value; measuring, by a second pH probe associated with the second vessel, a second pH value associated with the second vessel; comparing the second measured pH value associated with the second vessel to the known pH value of the equilibration buffer; determining whether the second measured pH value associated with the second vessel is different from the known pH value of the equilibration buffer by greater than a threshold pH value; and generating a second alert responsive to the second measured pH value associated with the second vessel being different from the known pH value of the equilibration buffer by greater than the threshold pH value.

For instance, in some examples, transferring the acidified pool from the first vessel to the second vessel based at least in part on receiving a signal indicating that the second vessel is empty.

Additionally, in some examples, filling the second vessel with the equilibration buffer is based at least in part on a receiving a signal indicating that the second vessel is empty.

Moreover, in some examples, the automated method of low pH viral inactivation may further include transferring the pool from the filter to a third vessel.

For instance, in some examples, transferring the pool from the filter to the third vessel is based at least in part on a receiving a signal indicating that the third vessel is empty.

Additionally, in some examples, the automated method of low pH viral inactivation may further include recalibrating the first pH probe responsive to the first alert. Similarly, in some examples, the automated method of low pH viral inactivation may further include recalibrating the second pH probe responsive to the second alert.

In still another aspect, a method for inactivating enveloped viruses during purification of a recombinant protein of interest is provided, the method comprising: obtaining a fluid known or suspected to contain at least one enveloped virus; subjecting the fluid to one or more of the following steps at a concentration and for a time sufficient to cause viral inactivation: adding the fluid to a first vessel; adding acid to the first vessel; measuring, by a first pH probe associated with the first vessel, a first pH value associated with the first vessel; ceasing, based on the first measured pH value associated with the first vessel being within a tolerance band of a target pH value for viral inactivation, the addition of acid to the first vessel; transferring the fluid from the first vessel to a second vessel; filling the first vessel with an equilibration buffer having a known pH value; measuring, by the first pH probe, a second pH value associated with the first vessel; comparing the second measured pH value associated with the first vessel to the known pH value of the equilibration buffer; determining whether the second measured pH value associated with the first vessel is different from the known pH value of the equilibration buffer by greater than a threshold pH value; and generating a first alert responsive to the second measured pH value associated with the first vessel being different from the known pH value of the equilibration buffer by greater than the threshold pH value; and subjecting the neutralized viral inactivated fluid to at least one unit operation which includes at least a filtration step or a chromatography step.

In some examples, adding the fluid to the first vessel is based in part on receiving a signal indicating that the first vessel is empty.

Additionally, in some examples, transferring the fluid from the first vessel to the second vessel is based in part on receiving a signal indicating that the second vessel is empty.

Moreover, in some examples, filling the first vessel with the equilibration buffer is based in part on receiving a signal indicating that the first vessel is empty.

Furthermore, in some examples, the fluid comprises a recombinant protein of interest. Moreover, in some examples, the fluid is harvested host cell culture fluid. Additionally, in some examples, the fluid is from an effluent stream, eluate, pool, storage or hold from a unit operation comprising a harvest step, a filtration step or a chromatography step. Furthermore, in some examples, the fluid is eluate collected from depth filtration, microfiltration, affinity chromatography, ion exchange chromatography, multimodal chromatography, hydrophobic interaction chromatography or hydroxyapatite chromatography. Additionally, in some examples, the fluid is a pool containing harvested cell culture fluid, eluate from depth filtration, eluate from microfiltration, eluate from affinity chromatography, eluate from ion exchange chromatography, eluate from multimodal chromatography, eluate from hydrophobic interaction chromatography, or eluate from hydroxyapatite chromatography. Furthermore, in some examples, the fluid is harvested host cell culture fluid and the unit operation includes depth filtration. Additionally, in some examples, the fluid is harvested host cell culture fluid and the unit operation includes microfiltration. Moreover, in some examples, the fluid is harvested host cell culture fluid and the unit operation includes Protein A affinity chromatography. Furthermore, in some examples, the fluid is Protein A eluant and the unit operation includes depth filtration.

Moreover, in some examples, the affinity chromatography is Protein A, Protein G, Protein A/G, or Protein L chromatography. Additionally, in some examples, the chromatography is selected from affinity chromatography, Protein A chromatography, ion exchange chromatography, anion exchange 20 chromatography, cation exchange chromatography; hydrophobic interaction chromatography; mixed modal or multimodal chromatography, or hydroxyapatite chromatography.

Additionally, in some examples, the unit operation includes depth filtration. Furthermore, in some examples, the unit operation includes microfiltration.

In another aspect, an automated system for low pH viral inactivation is provided, comprising: a first vessel; a second vessel; a first pH probe associated with the first vessel and configured to measure the pH of contents of the first vessel; a source of a fluid known or suspected to contain at least one enveloped virus to be transferred to the first vessel; an acid pump configured to pump acid into the first vessel after the fluid is transferred into the first vessel and configured to cease pumping acid into the first vessel responsive to the first pH probe measuring a first pH value that is within a tolerance band of a target pH value for viral inactivation; a transfer pump configured to pump the acidified pool from the first vessel to the second vessel responsive to the first pH probe measuring the first pH value that is below the threshold pH value for viral inactivation, and responsive to the acid pump ceasing to pump acid into the first vessel; a second pH probe associated with the second vessel and configured to measure the pH of contents of the second vessel; a base pump configured to pump base into the second vessel responsive to an elapsed time, from the entire acidified pool being pumped into the second vessel, exceeding a threshold amount of time for reducing a concentration of virus in the acidified pool to a predetermined safe level, and configured to cease pumping base into the second vessel responsive to the second pH probe measuring a first pH value that is within a threshold range of neutral pH values; and a discharge pump configured to pump the neutralized viral inactivated pool from the second vessel into a filter for treatment of the neutralized viral inactivated pool.

In some examples, the system includes a source pump configured to pump the fluid into the first vessel from the source based at least in part on a signal indicating that the first vessel is empty.

Furthermore, in some examples, the transfer pump is configured to pump the acidified pool from the first vessel to the second vessel based at least in part on a signal indicating that the second vessel is empty.

Moreover, in some examples, the automated system for low pH viral inactivation may further include a third vessel; and a collection pump configured to pump the filtered pool from the filter to the third vessel.

In some examples, the collection pump is configured to pump the filtered pool from the second vessel to the third vessel based at least in part on a signal indicating that the third vessel is empty.

Furthermore, in some examples, the automated system for low pH viral inactivation may further include one or more additional pH probes associated with the first vessel and configured to measure the pH of contents of the first vessel. Similarly, in some examples, the automated system for low pH viral inactivation may further include one or more additional pH probes associated with the second vessel and configured to measure the pH of contents of the second vessel.

Moreover, in some examples, the acid is selected from formic acid, acidic acid, citric acid, and phosphoric acid at concentrations suitable to ensure viral inactivation. Furthermore, in some examples, the threshold pH for viral inactivation is from pH 2 to 4. Additionally, in some examples, the chromatography elution pool is exposed to the acid for less than 30 minutes prior to neutralization. Moreover, in some examples, the base is Tris base at a concentration of 2M. Furthermore, in some examples, the threshold range of neutral pH values is from pH 4.5 to 6. Additionally, in some examples, the low pH viral inactivation is conducted at a temperature of 5 to 25° C.

Furthermore, in some examples, neutralized viral inactivated chromatography elution pool from the second vessel is transferred to a holding vessel. For instance, in some examples, the neutralized viral inactivated chromatography elution pool from the second vessel is transferred to a depth filter. Additionally, in some examples, following depth filtration, the neutralized viral inactivated eluate is transferred to a sterile filter. Moreover, in some examples, the neutralized viral inactivated chromatography elution pool from the second vessel is transferred a first polish chromatography column.

In still another aspect, an automated method of low pH viral inactivation is provided, the method comprising: adding a pool to a first vessel; adding acid to the first vessel; measuring, by a first pH probe associated with the first vessel, a first pH value associated with the first vessel; ceasing, based on the first measured pH value associated with the first vessel being within a tolerance band of a target pH value for viral inactivation, the addition of acid to the first vessel; transferring the pool from the first vessel to a second vessel; adding base to the second vessel after an elapsed time after the transfer of the pool to the second vessel exceeds a threshold amount of time for reducing a concentration of virus in the pool to a predetermined safe level; measuring, by a second pH probe associated with the second vessel, a first pH value associated with the second vessel; ceasing, based on the first measured pH value associated with the second vessel being within a threshold range of neutral pH values, the addition of base to the second vessel; and transferring the pool from the second vessel to a filter for treatment of the neutralized viral inactivated pool.

In some examples, transferring the pool into the first vessel is based at least in part on receiving a signal indicating that the first vessel is empty.

Furthermore, in some examples, transferring the acidified pool from the first vessel to the second vessel based at least in part on receiving a signal indicating that the second vessel is empty.

Moreover, in some examples, the automated method of low pH viral inactivation may further include transferring the pool from the filter to a third vessel.

For instance, in some examples, transferring the pool from the filter to the third vessel is based at least in part on a receiving a signal indicating that the third vessel is empty.

Additionally, in some examples, the automated method of low pH viral inactivation may further include recalibrating the first pH probe responsive to the first alert. Similarly, in some examples, the automated method of low pH viral inactivation may further include recalibrating the second pH probe responsive to the second alert.

In another aspect, a method for inactivating enveloped viruses during purification of a recombinant protein of interest is provided, comprising: obtaining a fluid known or suspected to contain at least one enveloped virus; subjecting the fluid to one or more of the following steps at a concentration and for a time sufficient to cause viral inactivation: adding the fluid to a first vessel; adding acid to the first vessel; measuring, by a first pH probe associated with the first vessel, a first pH value associated with the first vessel; ceasing, based on the first measured pH value associated with the first vessel being within a tolerance band of a target pH value for viral inactivation, the addition of acid to the first vessel; transferring the fluid from the first vessel to a second vessel; adding base to the second vessel; measuring, by a second pH probe associated with the first vessel, a second pH value associated with the second vessel; ceasing, based on the second measured pH value associated with the second vessel being within a tolerance band of a target pH value for neutrality, the addition of base to the second; and subjecting the neutralized viral inactivated fluid to at least one unit operation which includes at least a filtration step or a chromatography step.

In some examples, adding the fluid to the first vessel is based in part on receiving a signal indicating that the first vessel is empty.

Additionally, in some examples, transferring the fluid from the first vessel to the second vessel is based in part on receiving a signal indicating that the second vessel is empty.

Furthermore, in some examples, the fluid comprises a recombinant protein of interest. Moreover, in some examples, the fluid is harvested host cell culture fluid. Additionally, in some examples, the fluid is from an effluent stream, eluate, pool, storage or hold from a unit operation comprising a harvest step, a filtration step or a chromatography step. Furthermore, in some examples, the fluid is eluate collected from depth filtration, microfiltration, affinity chromatography, ion exchange chromatography, multimodal chromatography, hydrophobic interaction chromatography or hydroxyapatite chromatography. Additionally, in some examples, the fluid is a pool containing harvested cell culture fluid, eluate from depth filtration, eluate from microfiltration, eluate from affinity chromatography, eluate from ion exchange chromatography, eluate from multimodal chromatography, eluate from hydrophobic interaction chromatography, or eluate from hydroxyapatite chromatography. Furthermore, in some examples, the fluid is harvested host cell culture fluid and the unit operation includes depth filtration. Additionally, in some examples, the fluid is harvested host cell culture fluid and the unit operation includes microfiltration. Moreover, in some examples, the fluid is harvested host cell culture fluid and the unit operation includes Protein A affinity chromatography. Furthermore, in some examples, the fluid is Protein A eluant and the unit operation includes depth filtration.

Moreover, in some examples, the affinity chromatography is Protein A, Protein G, Protein A/G, or Protein L chromatography. Additionally, in some examples, the chromatography is selected from affinity chromatography, Protein A chromatography, ion exchange chromatography, anion exchange 20 chromatography, cation exchange chromatography; hydrophobic interaction chromatography; mixed modal or multimodal chromatography, or hydroxyapatite chromatography.

Additionally, in some examples, the unit operation includes depth filtration. Furthermore, in some examples, the unit operation includes microfiltration.

BRIEF DESCRIPTION OF THE DRAWINGS

The figures described below depict various aspects of the systems and methods disclosed herein. Advantages will become more apparent to those skilled in the art from the following description of the embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive. Further, wherever possible, the following description refers to the reference numerals included in the following figures, in which features depicted in multiple figures are designated with consistent reference numerals.

DETAILED DESCRIPTION

Figure 1A:
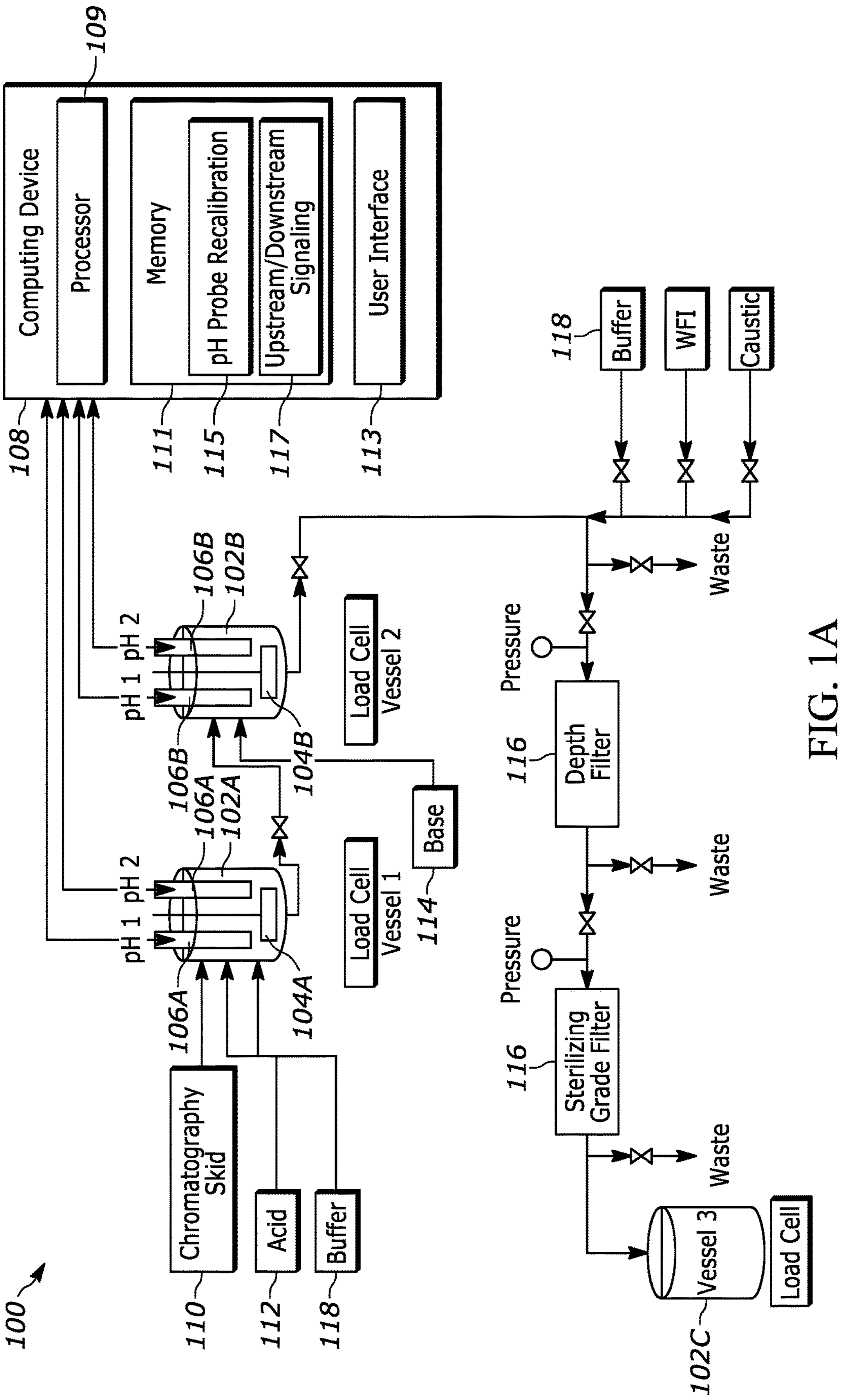
FIG. 1A illustrates a block diagram of an example automated system for low pH viral inactivation.

The inactivation of enveloped viruses known or suspected to be contained in a fluid can be performed by a number of different operations including heat inactivation/pasteurization, treatment with solvents and/or detergents, UV and gamma ray irradiation, use of high intensity broad spectrum white light, addition of chemical inactivating agents such as B-propiolactone, and/or low pH viral inactivation.

The present disclosure generally relates to an automated system and method for low pH viral inactivation. The automated system and method for low pH viral inactivation includes synchronization with the upstream and downstream units through its integration with the distributed control system, process control based on pool pH, and an automated viral inactivated pool filtration system.

For synchronization between the upstream and downstream units, communication to signal the status of the batches is necessary. There are two different types of synchronization strategies; synchronous and asynchronous. The synchronous strategy involves one unit sending a message to a secondary unit, and halting the process until the secondary unit confirms the message and sends a receipt back. In contrast, an asynchronous strategy does not require the process to halt for a confirmation message between the units and will continue on to its next step after the initial message is sent. In the automated system and method described herein, the synchronous communication system is utilized to prevent the upstream units from transferring the product pool into the downstream units before it is ready. The synchronization strategy also enables the system to allow variable number of cycles from the upstream chromatography by providing the option to process every eluate pool or collect multiple pools before processing. The automation is contained within the distributed control system and allows for supervisory control.

Generally speaking, a fluid known or suspected to contain at least one enveloped virus is added to a first vessel, and acid is added to the first vessel to lower the pH of the elution pool in the first vessel. Once pH probes in the first vessel measure a sufficiently low pH, the acidified fluid is transferred to a second vessel. The use of two vessels allows for the pool to first be brought down to the inactivation pH in the first vessel, and then transferred to the second vessel to be held for a validated inactivation time. This method eliminates the option for eluate drops to stick to the upper sides of the vessel walls during the hold period and miss the interaction with the acid, which would allow untreated pool drops to transfer through the process. With two vessels, all the contents from the pool that gets transferred to the second vessel are well mixed with the acid. Once the acidified fluid is held in the second vessel for the validated inactivation time, inactivating the virus to a predetermined safe level, the acidified fluid in the second vessel is neutralized. Generally speaking, there are two options for the acidification and neutralization strategy that can be chosen when creating the batch recipe: fixed and variable. Incremental dosing is utilized in both strategies, but when the fixed option is used, the doses of acid/base are constant, and when the variable option is used, the next dose is calculated based on the current pH of the pool and adjusted based on the result.

In any case, once the acidified fluid in the second vessel is neutralized, it is filtered through a combination depth and sterilization filtration system. A discharge pump and a series of valves are used to direct the cleaning solution, preparation buffer, and the product pool through the filters to a third vessel. The batch recipe on the distributed control system monitors and advances the filtration process without the need for operator involvement unless there is an alarm to be acknowledged. In existing systems, the inactivated product pool would have to be manually transferred to the filtration system. Advantageously, using the automated system and method described herein allows for a single closed system with the inactivation and filtration processes connected.

Meanwhile, once the acidified fluid is transferred from the first vessel to the second vessel, i.e., once the first vessel is emptied, a signal indicating that the first vessel is empty is sent upstream causing the first vessel to be immediately filled with an equilibration buffer at a known pH so that the pH probes remain wetted, and the reading from the pH probes in the first vessel is checked against this known pH to determine whether either of the pH probes need to be recalibrated. Generally speaking, each vessel contains at least two probes: a main probe that provides the pH reading and a back-up probe that can be used to as a redundant probe in case of failure of the main probe. In some cases, if the reading from a pH probe is different from the known pH by greater than a threshold amount, the pH probe may be automatically recalibrated, while in other cases, an alert may be generated to an operator who will recalibrate the pH probe.

Once the neutralized viral inactivated fluid is transferred from the second vessel to the third vessel, i.e., once the second vessel is emptied, a signal indicating that the second vessel is empty is sent upstream causing the second vessel to be immediately filled with an equilibration buffer at a known pH, and the pH probes of the second vessel are checked against the known pH to determine whether recalibration is needed. The process then repeats in a new cycle. That is, once the equilibration buffer is removed from the first vessel, i.e., once the first vessel is again emptied, a signal indicating that the first vessel is empty is sent upstream causing a new fluid known or suspected to contain at least one enveloped virus to be added to the first vessel. Acid is then added to the first vessel, and once the equilibration buffer is removed from the second vessel, i.e., once the second vessel is again emptied, a signal indicating that the second vessel is empty is sent upstream, causing the acidified pool to be added to the second vessel once pH probes in the first vessel measure a sufficiently low pH. That is, the acidified pool from the first vessel is added to the second vessel based on both signals: a signal indicating that the second vessel being empty, and a signal indicating that the pH probes in the first vessel measure a sufficiently low pH for viral inactivation.

Advantageously, using the automated system and method described herein, the pH probes of both vessels may remain immersed and wetted over multiple cycles, and their calibration status may be automatically assessed and corrected as needed without requiring operational staff to be constantly on hand to manually withdraw samples and measure the pH after each cycle. That is, rather than having a member of operational staff ready and waiting to check the calibration status of the pH probes before or after each cycle, operational staff may attend to other activities as needed, and may only need to intervene when alarms or alerts are generated. Beneficially, in some examples the pH probes of both vessels may remain accurate for use in many successive cycles of low pH viral inactivation without intervention from operational staff.

Accordingly, the use of the automated system and method may facilitate a reduction in operational staffing requirements, as it is capable of synchronizing with an upstream capture chromatography system to cycle independently and repeatedly. That is, operational staff reduction may be achieved by allowing the system to initiate cycles automatically, both by detecting the amount of product being collected from the capture chromatography step and by synchronizing communications with the chromatography system.

Referring now to the drawings, FIG. 1A illustrates a block diagram of an example automated system 100 for low pH viral inactivation. The system 100 includes a first vessel 102A, a second vessel 102B, and a third vessel 102C. The first vessel 102A and the second vessel 102B may each be equipped with respective agitators 104A and 104B configured to mix substances stored in the first vessel 102A and second vessel 102B respectively. Additionally, the first vessel 102A and the second vessel 102B may each be equipped with respective pH probes 106A and 106B configured to measure pH values associated with the first vessel 102A and the second vessel 102B respectively. While FIG. 1A illustrates two pH probes 106A associated with the first vessel 102A, and two pH probes 106B associated with the second vessel 102B, in some examples there may be one pH probe 106A or more than two pH probes 106A associated with the first vessel 102A (and in some examples, there may be one pH probe 106B or more than two pH probes 106B associated with the second vessel 102B). The system 100 further includes a computing device 108 configured to interface with the pH probes 106A and 106B. The computing device 108 may include one or more processors 109 and a respective a memory 111 (e.g., volatile memory, non-volatile memory) accessible by one or more processors 109 (e.g., via a memory controller), as well as a user interface 113. The one or more processors 109 may interact with the memory 111 to execute computer-readable instructions stored in the memory 111. The computer-readable instructions stored in the memory 111 may cause the one or more processors 110 to execute a pH probe recalibration application 115 and an upstream/downstream signaling application 117.

The system 100 further includes a chromatography skid 110, one or more vessels 112 or other containers for acid, one or more vessels 114 or other containers for base, one or more filters 116 (such as a depth filter, a sterilizing grade filter, etc.), one or more vessels 118 or other containers for buffer. Additionally, the system 100 may include one or more pumps, valves, or other means for transferring liquids between these various vessels or other containers and through the filters. For example, the system 100 may include one or more pumps, valves, or other means for transferring a fluid known or suspected to contain at least one enveloped virus from the chromatography skid 110 to the first vessel 102A continuously or intermittently. In some examples, the pumps and/or valves may transfer the fluid from the chromatography skid 110 to the first vessel 102A only upon receiving an upstream signal from the upstream/downstream signaling application 117 indicating that the first vessel 102A is currently empty. Furthermore, the system 100 may include one or more pumps, valves, or other means for transferring acid from the vessel 112 to the first vessel 102A. In some examples, the pumps and/or valves may transfer the acid from the vessel 112 to the first vessel 102A only upon receiving an upstream signal from the upstream/downstream signaling application 117 indicating that the first vessel 102A currently contains the fluid known or suspected to contain the virus. The agitator 104A may mix the acid with the fluid known or suspected to contain at least one enveloped virus (and/or additional acid may be added to the elution pool) until the pH probe(s) 106A associated with the first vessel 102A measures a pH value below a predetermined threshold pH value (e.g., a pH value of 3.5-3.7) for the inactivation of enveloped viruses in the fluid.

Additionally, the system 100 may include one or more pumps, valves, or other means for transferring the acidified fluid from the first vessel 102A to the second vessel 102B once the pH probe(s) 106A associated with the first vessel 102A measures a pH value below the predetermined threshold pH value. In some examples, the pumps and/or valves may transfer the acidified fluid from the first vessel 102A to the second vessel 102B only upon receiving an upstream signal from the upstream/downstream signaling application 117 indicating that the second vessel 102B is currently empty. Once transferred into the second vessel 102B, the acidified fluid may remain in the second vessel 102B for a predetermined period of time (e.g., a period of ≤30 minutes) sufficient to reduce the concentration of virus in the acidified elution pool to below a predetermined safe level (e.g., a level set by a regulatory agency related to a drug to be made from the fluid known or suspected to contain at least one enveloped virus, in addition to a recombinantly produced therapeutic protein).

Figure 1B:
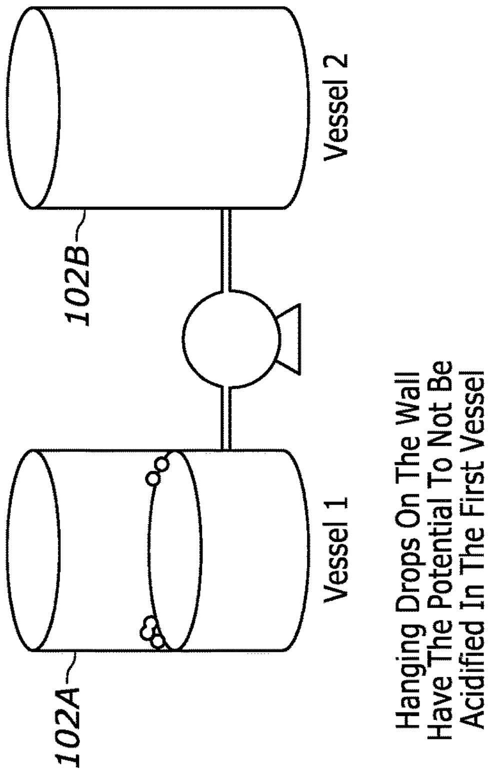
FIGS. 1B and 1C illustrate an example of how a two-vessel design may be used to prevent hanging drops in the example automated system for low pH viral inactivation of FIG. 1A.
Figure 1C:
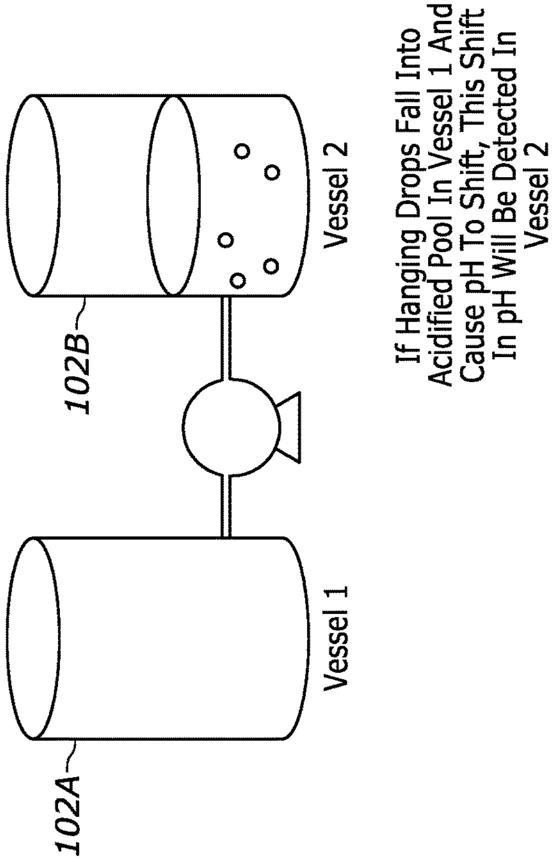

For instance, as shown in FIGS. 1B and 1C, transferring the acidified fluid from the first vessel 102A (as shown in FIG. 1B) to the second vessel 102B (as shown in FIG. 1C) in this manner allows for the pool to first be brought down to the inactivation pH in the first vessel 102A, and then transferred to the second vessel 102B to be held for the validated inactivation time. By holding the pool in the second vessel 102B for the validated inactivation time, rather than holding the pool in the first vessel 102A for the validated inactivation time, the system 100 eliminates the option for eluate drops to stick to the upper sides of the walls of the first vessel 102A during the hold period and miss the interaction with the acid, which would allow untreated pool drops to transfer through the process. That is, by using two vessels 102A and 102B, all the contents from the pool that gets transferred from the first vessel 102A to the second vessel 102B are well mixed with the acid.

Referring back to FIG. 1A, one or more pumps or valves of the system 100 may transfer base from the vessel or other container 114 to the second vessel 102B. In some examples, the pumps and/or valves may transfer base from the vessel or other container 114 to the second vessel 102B only upon receiving an upstream signal from the upstream/downstream signaling application 117 indicating that the second vessel 102B currently contains the acidified (or viral inactivated) fluid. The agitator 104B may mix the base with the acidified (or viral inactivated) fluid (and/or additional acid may be added to the elution pool) until the pH probe(s) 106B associated with the second vessel 102B measures a neutral pH value (e.g., a pH value of 5.0-6.0). Furthermore, the system 100 may include one or more pumps, valves, or other means for transferring the neutralized viral inactivated fluid from the second vessel 102B through one or more filters 116 (such as a depth filter and a sterilizing grade filter) and to transfer the filtered neutralized viral inactivated fluid to the third vessel 102C where it can be collected for use. In some examples, the pumps and/or valves may transfer the neutralized viral inactivated fluid from the second vessel 102B through one or more filters 116 to the third vessel 102C only upon receiving an upstream signal from the upstream/downstream signaling application 117 indicating that the third vessel 102C (and/or the filters 116) are currently empty.

Meanwhile, immediately after the acidified fluid has been transferred out of the first vessel 102A, the upstream/downstream signaling application 117 may send an upstream signal indicating that the first vessel 102A has been emptied to one or more pumps or valves of the system 100, causing the transfer of an equilibration buffer having a known pH from a vessel 118 into the first vessel 102A such that the pH probes 106A remain wetted. At this point, the pH probes 106A may measure the pH of the equilibration buffer in the first vessel 102A and send an indication of the measured pH to the computing device 108, where the pH probe recalibration application 115 may compare the measured pH of the equilibration buffer in the first vessel 102A to the known pH of the equilibration buffer. If the pH probe recalibration application 115 determines that the measured pH differs from the known pH of the equilibration buffer by greater than a threshold pH value (e.g., greater than 0.1 pH units), the pH probe recalibration application 115 may generate an alert indicating that the pH probe 102A (or a particular one of the pH probes 102A) needs to be recalibrated. The computing device 108 may display or otherwise convey the alert to an operator via the user interface 113. Additionally, in some examples, the pH probe recalibration application 115 may cause the computing device 108 to generate a control signal causing the pH probe 102A (or a particular one of the pH probes 102A) to be automatically recalibrated based on the known pH of the equilibration buffer, e.g., causing an adjustment such that the pH probe 102A, when measuring the pH of the equilibration buffer, measures a pH value within +/−0.1 pH units of the known pH of the equilibration buffer.

Similarly, immediately after the neutralized viral inactivated fluid has been transferred out of the second vessel 102B, the upstream/downstream signaling application 117 may send an upstream signal indicating that the second vessel 102B has been emptied to one or more pumps or valves of the system 100, causing the transfer of an equilibration buffer having a known pH from one of the vessels 118 (which may or may not be the same equilibration buffer used with the first vessel 102A) into the second vessel 102B such that the pH probes 106B remain wetted. At this point, the pH probes 106B may measure the pH of the equilibration buffer in the second vessel 102B and send an indication of the measured pH to the computing device 108, where the pH probe recalibration application 115 may compare the measured pH of the equilibration buffer in the second vessel 102B to the known pH of the equilibration buffer. If the pH probe recalibration application 115 determines that the measured pH differs from the known pH of the equilibration buffer by greater than a threshold pH value (e.g., greater than 0.1 pH units), the pH probe recalibration application 115 may generate an alert indicating that the pH probe 102B (or a particular one of the pH probes 102B) needs to be recalibrated. The computing device 108 may display or otherwise convey the alert to an operator via the user interface 113. Additionally, in some examples, the pH probe recalibration application 115 may cause the computing device 108 to generate a control signal causing the pH probe 102B (or a particular one of the pH probes 102B) to be automatically recalibrated based on the known pH of the equilibration buffer, e.g., causing an adjustment such that the pH probe 102B, when measuring the pH of the equilibration buffer, measures a pH value within +/−0.1 pH units of the known pH of the equilibration buffer.

Figure 2:
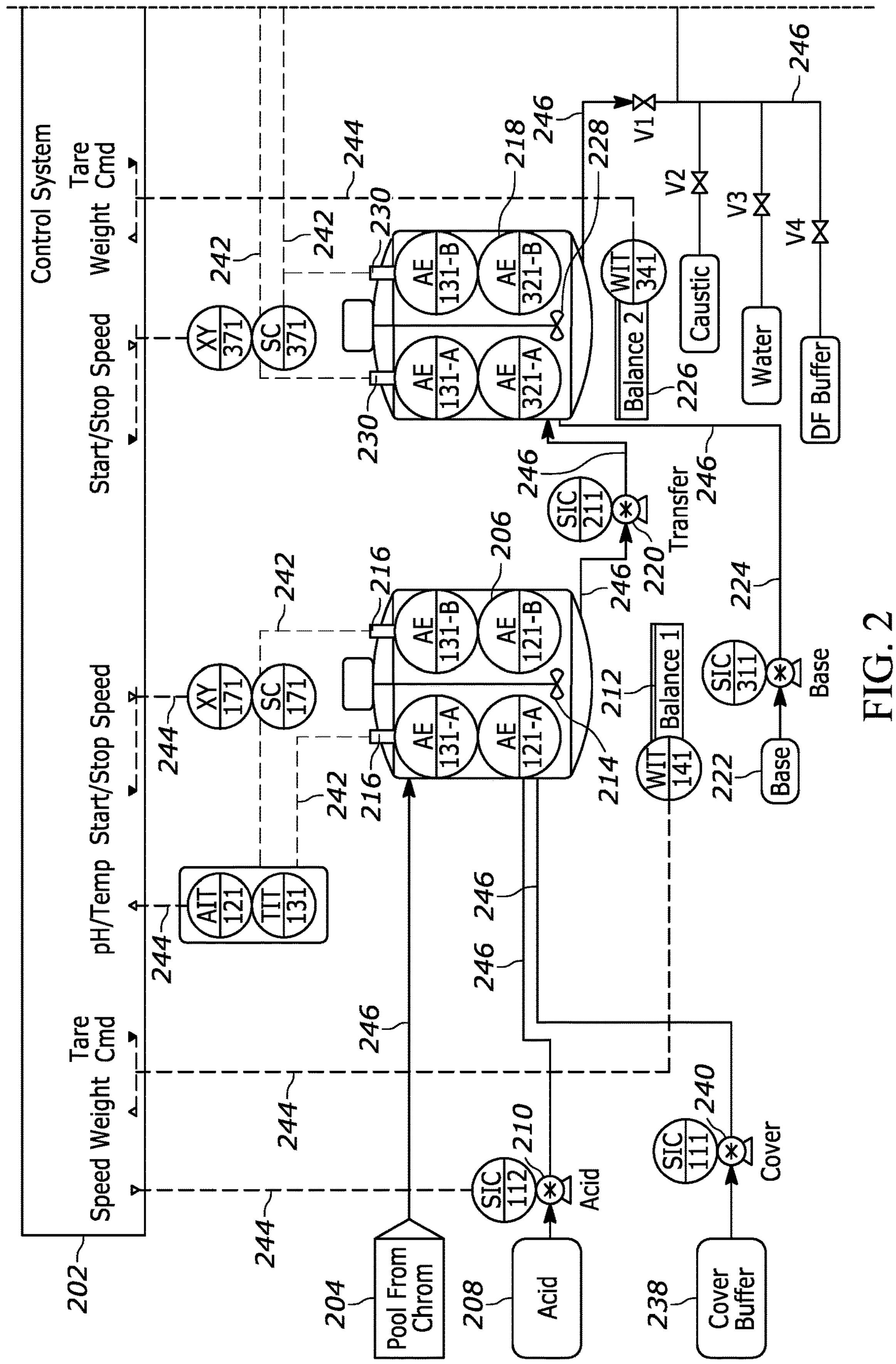
FIG. 2 illustrates a piping and instrumentation diagram (P&ID) of an example automated system for low pH viral inactivation.
Figure 2:
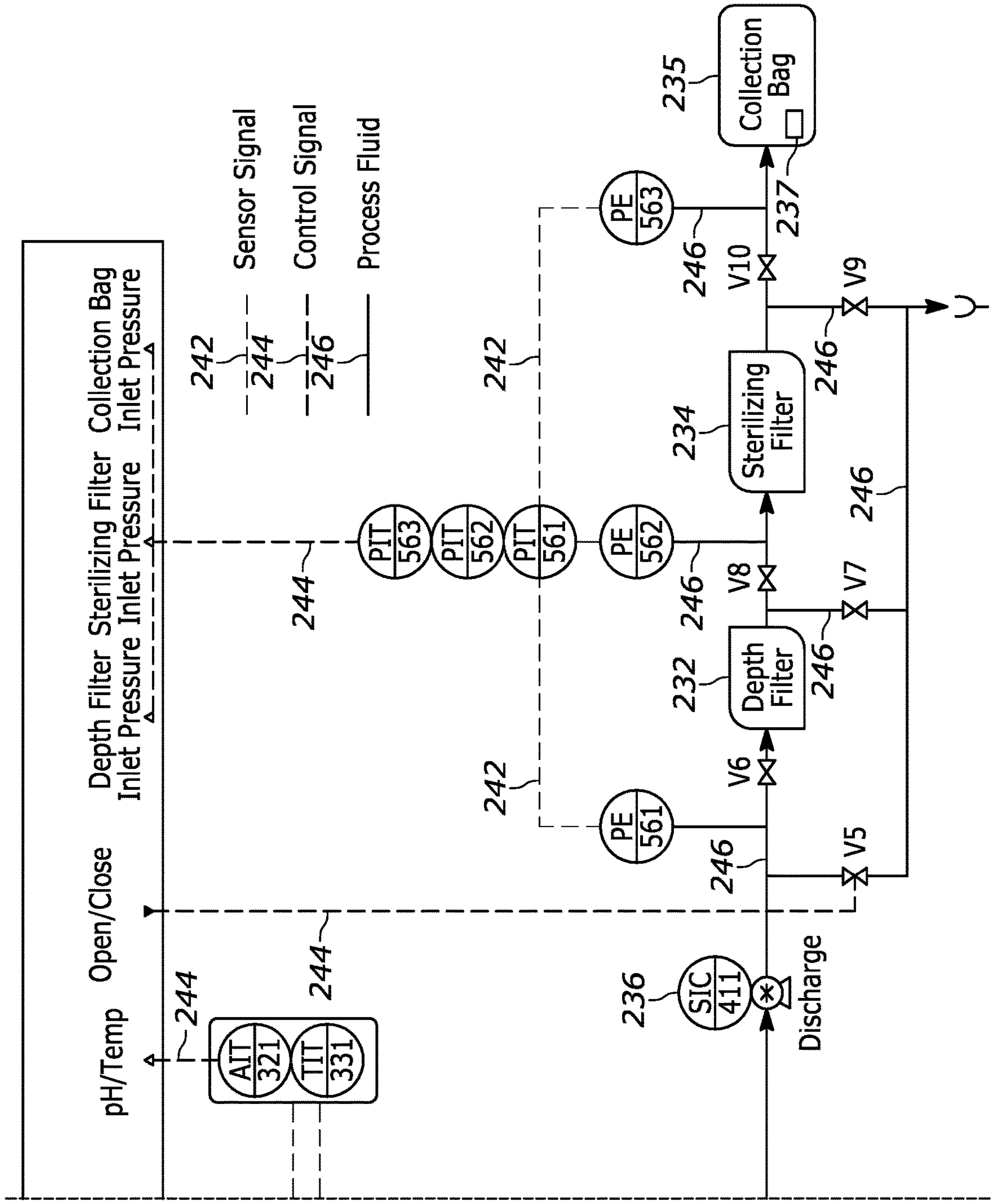

Referring now to FIG. 2, the piping and instrumentation diagram (P&ID) 200 of the example automated system for low pH viral inactivation illustrates the piping and process equipment of the system together with the instrumentation and control devices of this system. FIG. 2 illustrates fluidly connected components (i.e., components between which fluids can flow) with solid lines 246, and illustrates communicatively connected components with dashed lines. In particular, short-dashed lines 242 between two components indicate that sensor signals may be sent and/or received between the two components, while long-dashed lines 244 between two components indicate that control signals may be sent and/or received between the two components.

As shown in FIG. 2, a control system 202 (which may be or may include the computing device 108 illustrated with respect to FIG. 1A in some examples, and may include additional or alternative computing devices in some examples) is communicatively connected to various components of the system to receive sensor signals and to send control signals in order to operate the automated system for low pH viral inactivation in accordance with the information disclosed herein. While certain indications of control and sensor signals sent and received by the control system 202 are illustrated in FIG. 2, FIG. 2 may not necessarily show every control and sensor signal that may be sent by the control system 202, for simplicity of the diagram. That is, the control system 202 may send and/or receive additional or alternative control and/or sensor signals in order to operate the automated system for low pH viral inactivation in accordance with the information provided herein.

For instance, a chromatography skid 204 may be fluidly connected to a first vessel 206, such that a fluid known or suspected to contain at least one enveloped virus may be transferred from the chromatography skid 204 to the first vessel 206. A vessel or other container 208 containing acid may also be fluidly connected to the first vessel 206. As shown in FIG. 2, an acid pump 210 may be fluidly connected to the acid vessel 208 and the first vessel 204, and may pump acid from the acid vessel 208 to the first vessel 204. In some examples, the control system 202 may send control signals to the acid pump 210, e.g., in order to control the speed of the acid pump 210 and/or the amount of acid pumped into the first vessel 204 as described herein. Furthermore, in some examples, a weighing scale 212 may capture indications of the weight of the first vessel 206 and the fluids within the first vessel 204, and may send these indications to the control system 202. In some examples, the control system 202 may determine whether the first vessel 206 is full or empty based on the signal from the weighing scale 212, and may control when the enveloped virus is transferred from the chromatography skid 204 into the first vessel 206 (and/or when the acid pump 210 transfers acid into the first vessel 206, when the buffer pump 240 pumps buffer into the first vessel 206, etc.) based on whether the first vessel 206 is full or empty. Furthermore, in some examples, the control system 202 may control the speed of the acid pump 210 based on the combined weight of the acid and the fluid known or suspected to contain at least one enveloped virus within the first vessel 206. Additionally, in some examples, the control system 202 may send control signals to an agitator 214 within the first vessel 206 so that the agitator 214 mixes the acid and the fluid known or suspected to contain at least one enveloped virus in the first vessel 206 at speeds and/or positions as described herein.

One or more pH probes 216 positioned within (or otherwise associated with) the first vessel 206 may be configured to measure the pH of contents of the first vessel (e.g., the acidified fluid mixed in the first vessel 206 by the agitator 214) and send sensor signals to the control system 202 indicating the measured pH value or values associated with the first vessel 206.

The first vessel 206 may be fluidly connected to a second vessel 218 such that the acidified fluid may be transferred from the first vessel 206 to the second vessel 218. A transfer pump 220 may be fluidly connected to the first vessel 206 and the second vessel 218, and may pump the acidified fluid from the first vessel 206 to the second vessel 218, e.g., based on control signals received from the control system 202. For instance, the control system 202 may control the transfer pump 220 to pump the acidified fluid from the first vessel 206 to the second vessel 218 based on sensor data the control system 202 receives from other components (e.g., starting at a time based on the pH measured by the pH probes 216 reaching a target pH value for killing viruses, starting at a time based on the elapsed time reaching a target total time for acidification, and/or pumping at a rate or speed based on a target transfer time from the first vessel 206 to the second vessel 218).

A vessel or other container 222 containing base may be fluidly connected to the second vessel 218 such that the base may be transferred from the base vessel 222 to the second vessel 218. A base pump 224 may be fluidly connected to the base vessel 222 and the second vessel 218, and may pump the base from the first vessel 206 to the second vessel 218, e.g., based on control signals received from the control system 202. For instance, the control system 202 may send control signals to control the base pump 224 as it pumps base from the base vessel 222 to the second vessel 218, e.g., controlling the speed or rate of the base pump 224 and/or the amount of base pumped into the second vessel 218 as described herein. Furthermore, in some examples, a weighing scale 226 may capture indications of the weight of the second vessel 218 and the fluids within the first vessel 218, and may send these indications to the control system 202. In some examples, the control system 202 may determine whether the second vessel 218 is full or empty based on the signal from the weighing scale 226, and may control when the acidified fluid from the first vessel 206 is transferred into the second vessel 218 (and/or when the base pump 224 transfers base into the second vessel 218, when the buffer pump 240 pumps buffer into the second vessel 218, etc.) based on whether the second vessel 218 is full or empty. Furthermore, in some examples, the control system 202 may control the speed of the base pump 224 based on the combined weight of the base and the fluid known or suspected to contain at least one enveloped virus within the second vessel 218. Additionally, in some examples, the control system 202 may send control signals to an agitator 228 within the second vessel 218 so that the agitator 228 mixes the base and the fluid known or suspected to contain at least one enveloped virus in the second vessel 218 at speeds and/or positions as described herein.

One or more pH probes 230 positioned within (or otherwise associated with) the second vessel 218 may be configured to measure the pH of contents of the second vessel (e.g., the neutralized viral inactivated fluid mixed in the second vessel 218 by the agitator 228) and send sensor signals to the control system 202 indicating the measured pH value or values associated with the second vessel 218.

The second vessel 218 may be fluidly connected to a series of filters including a depth filter 232 and a sterilizing filter 234. A discharge pump 236 may be fluidly connected to the second vessel 218 and the filters 232, 234, and may pump the neutralized viral inactivated fluid from the second vessel 218 through the filters 232, 234 and into a third vessel 235, e.g., based on control signals received from the control system 202. In some examples, the third vessel 235 may be a collection bag. Additionally, in some examples, the third vessel 235 may include a load cell 237 configured to measure the weight of the load cell and generate an upstream or downstream signal indicating that the third vessel 235 is full.

For instance, the control system 202 may control the discharge pump 236 to pump the neutralized viral inactivated fluid from the second vessel 218 to the filters 232, 234 based on sensor data the control system 202 receives from other components (e.g., starting at a time based on the pH measured by the pH probes 230 reaching a target neutralization pH value, starting at a time based on the elapsed time reaching a target total time for neutralization, and/or pumping at a rate or speed based on a target filtration flow rate). Additionally, the control system 202 may receive sensor data from sensors associated with the filters 232, 234, and may control the filters 232, 234 (i.e., based on the sensor data) to operate in accordance with the filtration specifications and requirements described herein.

Additionally, a vessel or other container 238 containing buffer may be fluidly connected to the first vessel 206 and/or the second vessel 218 such that buffer may be transferred from the buffer vessel 238 to the first vessel 206 and/or the second vessel 218. In some examples, the buffer vessel 238 may be fluidly connected to the first vessel 206 and the second vessel such that buffer may be transferred from the buffer vessel to the first vessel, and then subsequently transferred to the second vessel (e.g., via the transfer pump 220). A buffer pump 240 may be fluidly connected to the buffer vessel 238 and the first vessel 206 and/or the second vessel 218, and may pump the buffer from the buffer vessel 238 to the first vessel 206 and/or the second vessel 218 based on control signals received from the control system 202. In particular, the control system 202 may control the buffer pump 240 to pump buffer into the first vessel 206 and into the second vessel 218 after the fluid known or suspected to contain at least one enveloped virus has been transferred out of each of the first vessel 206 and the second vessel 218, respectively, in accordance with the filtration specifications and requirements. That is, as discussed above, the buffer, which may have a known pH value, and may be pumped into the first vessel 206 after the acidified fluid is pumped from the first vessel 206 to the second vessel 218. Similarly, the buffer may be pumped into the second vessel 218 after the neutralized viral inactivated fluid is pumped from the second vessel 218 through the filters 232 and 234 and into the third vessel 235. The pH probes 216 and 230 may each measure the pH value of the buffer when the buffer is pumped into the respective first vessel 206 and second vessel 218. The pH probes 216 and 230 may send an indication of their respective measured pH values for the buffer to the control system 202, which may compare the measured pH values for the buffer to the known pH of the buffer to determine whether any recalibration of any of the pH probes 216 or 230 is needed. In some cases, the control system 202 may send control signals to any of the pH probes needing recalibration as needed in order to recalibrate the probes. Moreover, in some cases, the control system 202 may generate an alert for an operator indicating which pH probes, if any, need to be recalibrated.

After any recalibration of the probes 216 is complete, the transfer pump 220 may pump the buffer out of the first vessel 206, and a new fluid known or suspected to contain at least one enveloped virus from the chromatography skid 204 may be pumped or otherwise transferred into the first vessel in order to start a new cycle of automated viral inactivation. Similarly, after any recalibration of the probes 230 is complete, the discharge pump 236 may pump the buffer out of the second vessel 218, and the transfer pump 220 may pump a newly acidified fluid from the first vessel 206 into the second vessel 218. Accordingly, the system may proceed through a new cycle of automated viral inactivation after recalibrating the probes 216 and 230 as needed.

Figure 3:
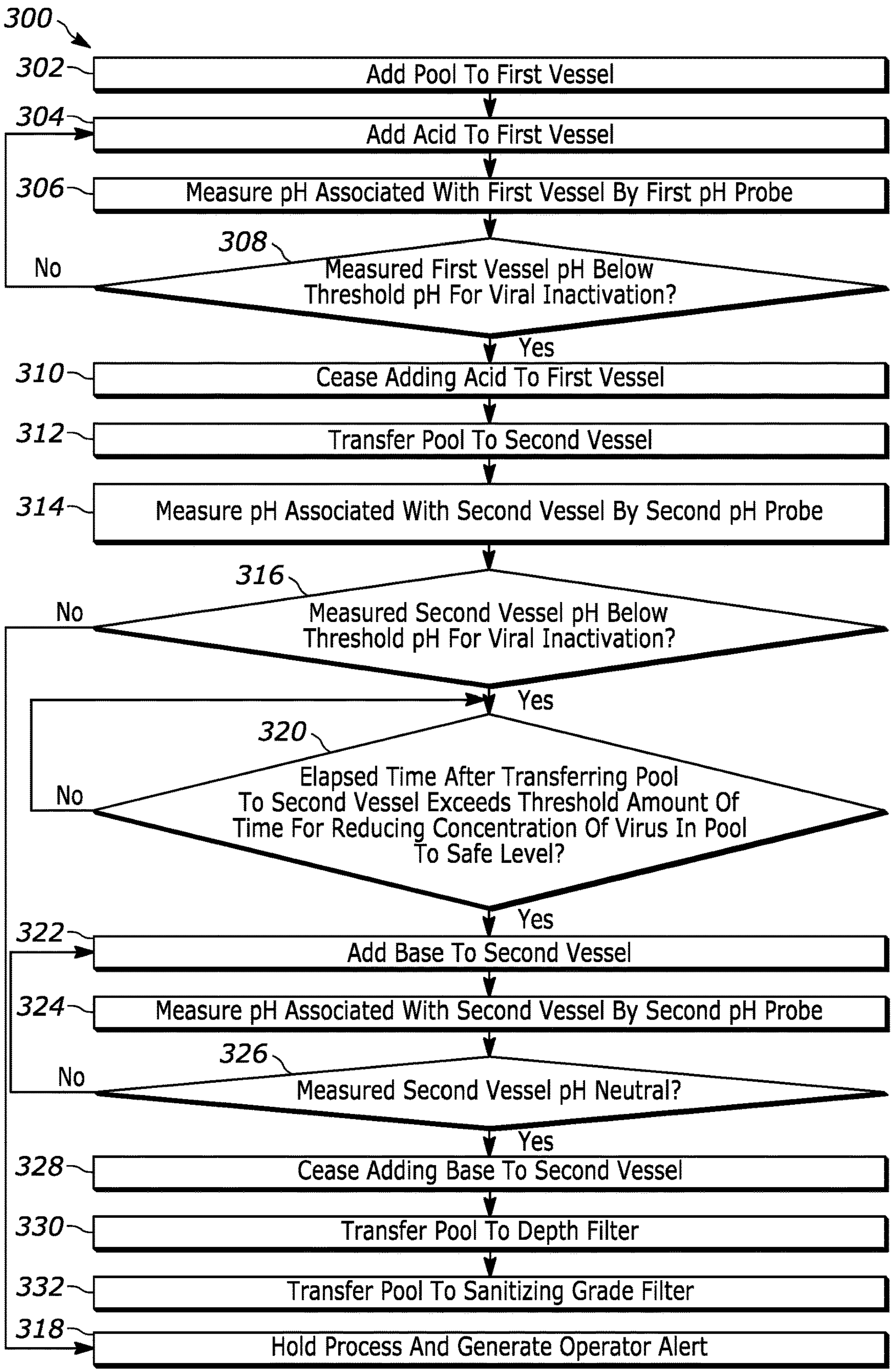
FIG. 3 illustrates a flow diagram associated with an example automated method of low pH viral inactivation using a fluid known or suspected to contain at least one enveloped virus.

FIG. 3 illustrates a flow diagram associated with an example automated method 300 of low pH viral inactivation using a fluid known or suspected to contain at least one enveloped virus. The method 300 may begin when a chromatography elution pool is added (block 302) to a first vessel. Acid may be added (block 304) to the first vessel and mixed with the fluid known or suspected to contain at least one enveloped virus (e.g., by an agitator of the first vessel) to acidify the fluid. A first pH probe associated with the first vessel may measure (block 306) a pH value associated with the first vessel. The method may include determining (block 308) whether the measured pH value is below a threshold pH value (or is within a range of pH values) associated with viral inactivation. If the pH value measured by the first pH probe associated with the first vessel is not below the threshold pH value (or not within the range of pH values) for viral inactivation (block 308, NO), additional acid may be added to the first vessel (block 304), or the acid may be kept in the first vessel for an additional period of time before measuring the pH of the first vessel again (block 306). If the pH value measured by the first pH probe associated with the first vessel is below the threshold pH value (or within the range of pH values) for viral inactivation (block 308, YES), the addition of acid to the first vessel may be ceased (block 310), and the acidified fluid may be transferred (block 312) to a second vessel.

A second pH probe associated with the second vessel may measure (block 314) a pH value associated with the first vessel. The method may include determining (block 316) whether the measured pH value is below a threshold pH value (or is within a range of pH values) associated with viral inactivation. If the pH value measured by the second pH probe associated with the second vessel is not below the threshold pH value (or not within the range of pH values) for viral inactivation (block 316, NO), the process may be held (block 318), and an alert may be generated for an operator, e.g., to prompt an operator to investigate any issues with the measured pH. If the pH value measured by the second pH probe associated with the second vessel is below the threshold pH value (block 316, YES), the method may proceed to block 320, where a determination may be made as to whether an elapsed time after transferring the acidified fluid from the first vessel to the second vessel has exceeded a threshold amount of time (e.g., ≤30 minutes) for inactivating a concentration of virus in the fluid to a predetermined safe level. If not (block 320, NO), the determination at block 314 may be made again after additional elapsed time. If so (block 320, YES), the method may proceed to block 322, where base may be added to the second vessel to neutralize the acidified fluid.

The second pH probe associated with the second vessel may again measure (block 324) a pH value associated with the second vessel, and a determination may be made as to whether the measured pH value associated with the second vessel is within an acceptable range of neutral pH values (e.g., a pH value range of 5.0-6.0). If the measured pH value associated with the second vessel is not within the acceptable range (block 326, NO), additional base may be added (block 322) to the vessel. If the measured pH value associated with the second vessel is within the acceptable range (block 326, YES), the addition of base to the second vessel may be ceased (block 328), and the neutralized viral inactivated fluid may be transferred (block 330) to a depth filter, and then transferred (block 332) to a sanitizing grade filter.

Figure 4A:
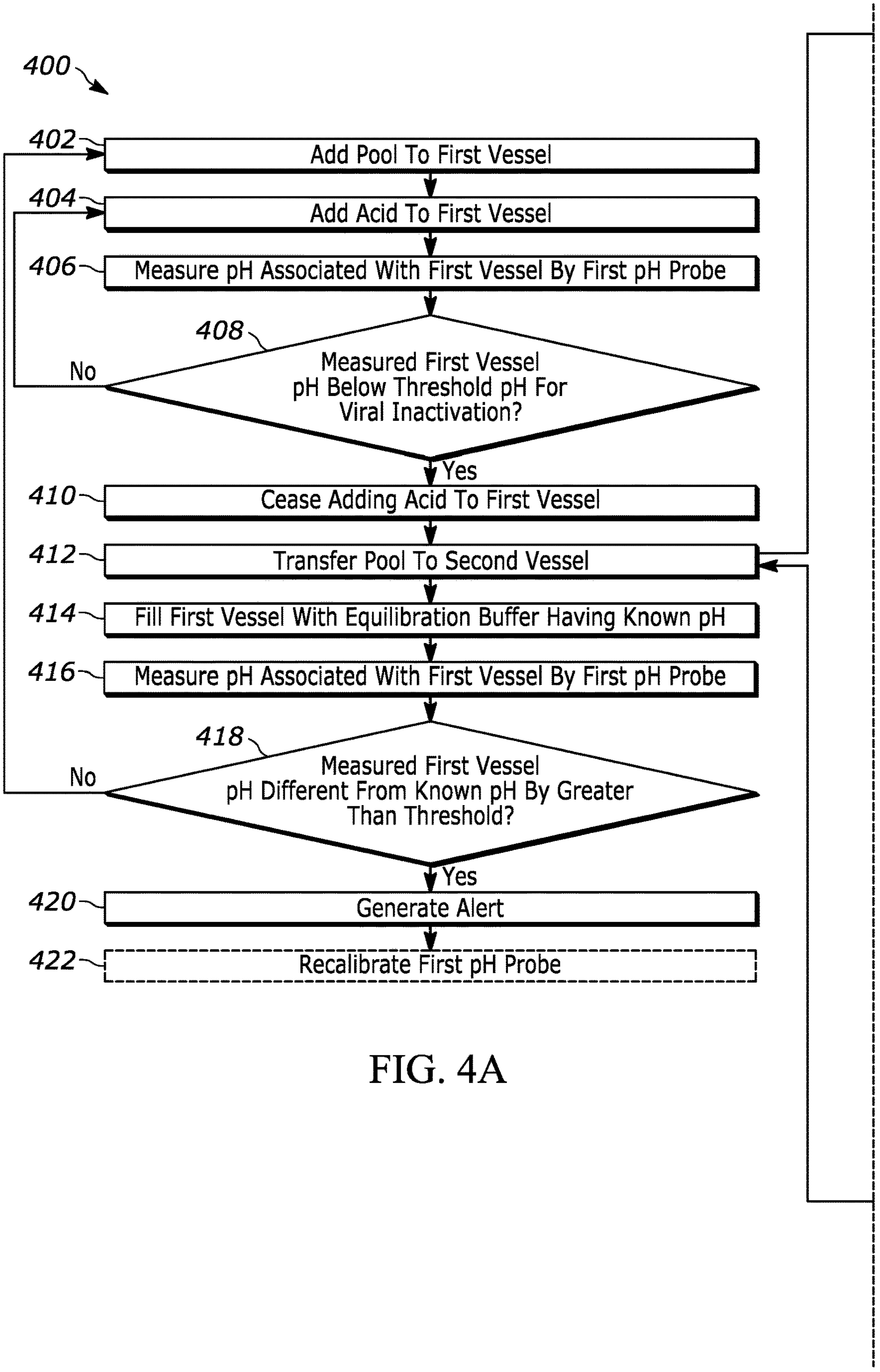
FIGS. 4A-4B illustrate a flow diagram associated with an example automated method of low pH viral inactivation using a fluid known or suspected to contain at least one enveloped virus, including automated cycles of pH probe calibration.
Figure 4B:
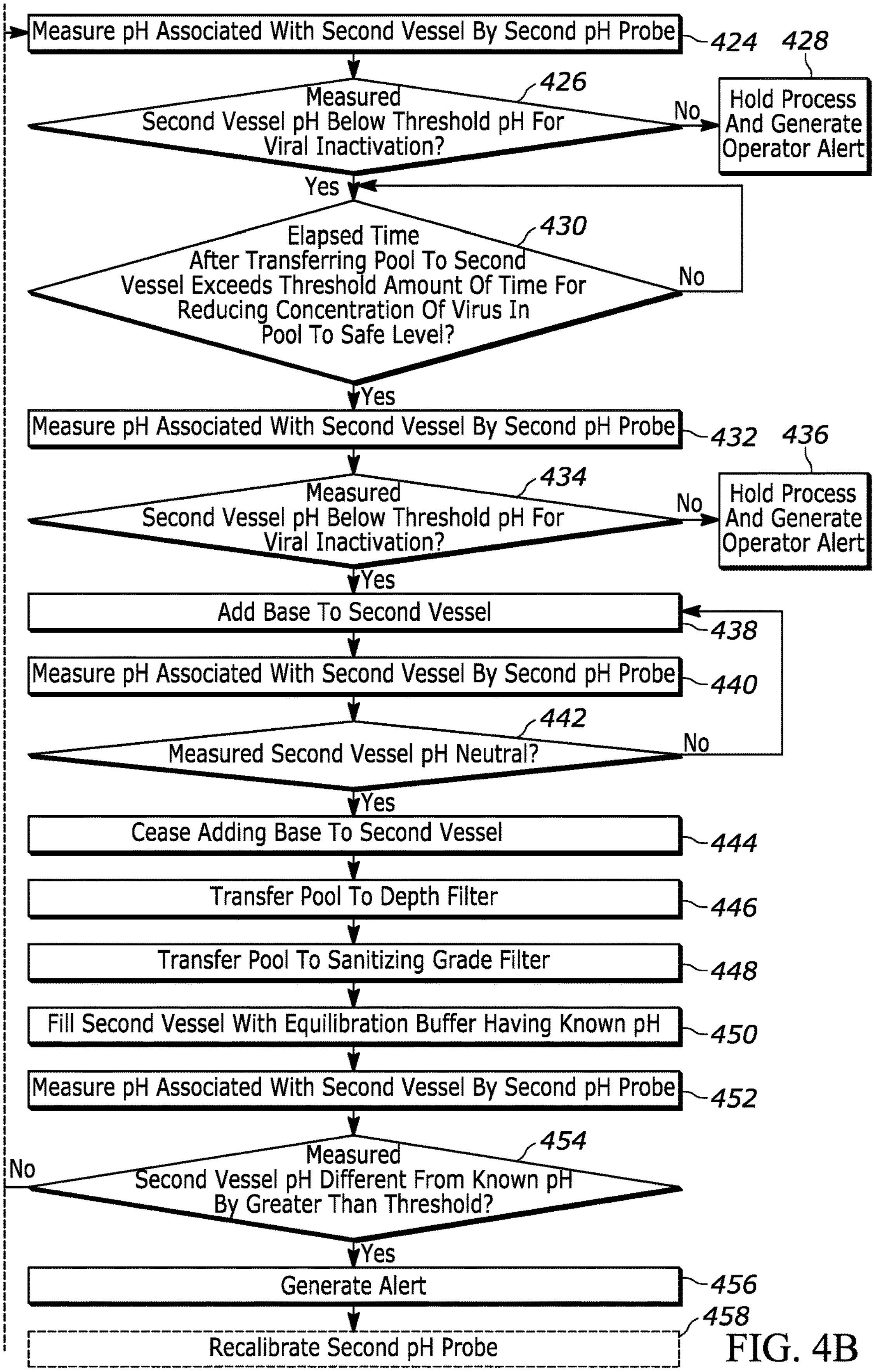

Referring now to FIGS. 4A-4B, a flow diagram associated with an example automated method 400 of low pH viral inactivation, including automated cycles of pH probe calibration, is illustrated. The method 400 may begin when a chromatography elution pool is added (block 402) to a first vessel. Acid may be added (block 404) to the first vessel and mixed with the fluid known or suspected to contain at least one enveloped virus (e.g., by an agitator of the first vessel) to acidify the fluid. A first pH probe associated with the first vessel may measure (block 406) a pH value associated with the first vessel. The method may include determining (block 408) whether the measured pH value is below a threshold pH value (or is within a range of pH values) associated with viral inactivation. If the pH value measured by the first pH probe associated with the first vessel is not below the threshold pH value (or not within the range of pH values) for viral inactivation (block 408, NO), additional acid may be added to the first vessel (block 404), or the acid may be kept in the first vessel for an additional period of time before measuring the pH of the first vessel again (block 406). If the pH value measured by the first pH probe associated with the first vessel is below the threshold pH value (or within the range of pH values) for viral inactivation (block 408, YES), the addition of acid to the first vessel may be ceased (block 410), and the acidified fluid may be transferred (block 412) to a second vessel. In some examples, the method 400 may proceed from block 412 to block 424, as discussed in greater detail below with respect to FIG. 4B. In any case, the method 400 may proceed from block 412 to block 414.

The first vessel may be filled (block 414) with an equilibration buffer having a known pH, and the pH associated with the first vessel may be measured (block 416) by the first pH probe associated with the first vessel. This measured pH value associated with the first vessel may be compared (block 418) to the known pH value of the equilibration buffer to determine whether the measured pH value associated with the first vessel is different from the known pH value of the equilibration buffer by greater than a threshold pH value (e.g., by more than 0.1 pH units). If the measured pH value associated with the first vessel is within 0.1 pH units of the known pH value of the equilibration buffer (block 418, NO), the method 400 may end or may proceed to block 402 to begin a new viral inactivation cycle by adding a new fluid known or suspected to contain at least one enveloped virus to the first vessel (after dumping the equilibration buffer from the first vessel).

If the pH probe's measured pH value associated with the first vessel is not within 0.1 pH units of the known pH value of the equilibration buffer (block 418, YES), an alert may be generated (block 420) indicating that the pH probe should be recalibrated. In some examples, the method 400 may include displaying or otherwise conveying the alert to an operator (e.g., via a user interface display) so that the operator can manually recalibrate the pH probe as needed. Moreover, in some examples, the method may include automatically recalibrating (block 422) the pH probe such that the pH probe measures a pH within 0.1 pH units of the equilibration buffer.

Referring now to FIG. 4B, as discussed above, the method 400 may include proceeding from block 412 to block 424.

A second pH probe associated with the second vessel may measure (block 424) a pH value associated with the first vessel. The method may include determining (block 426) whether the measured pH value is below a threshold pH value (or is within a range of pH values) associated with viral inactivation. If the pH value measured by the second pH probe associated with the second vessel is not below the threshold pH value (or not within the range of pH values) for viral inactivation (block 426, NO), the process may be held (block 428), and an alert may be generated for an operator, e.g., to prompt an operator to investigate any issues with the measured pH. If the pH value measured by the second pH probe associated with the second vessel is below the threshold pH value (block 426, YES), the method may proceed to block 430, where a determination may be made as to whether an elapsed time after transferring the acidified fluid from the first vessel to the second vessel has exceeded a threshold amount of time (e.g., ≤30 minutes) for inactivating a concentration of virus in the fluid to a predetermined safe level. If not (block 430, NO), the determination at block 430 may be made again after additional elapsed time. If so (block 430, YES), the second pH probe associated with the second vessel may again measure (block 432) a pH value associated with the first vessel. The method may include determining (block 434) whether the measured pH value is below a threshold pH value (or is within a range of pH values) associated with viral inactivation. If the pH value measured by the second pH probe associated with the second vessel is not below the threshold pH value (or not within the range of pH values) for viral inactivation (block 434, NO), the process may be held (block 436), and an alert may be generated for an operator, e.g., to prompt an operator to investigate any issues with the measured pH.

If the pH value measured by the second pH probe associated with the second vessel is below the threshold pH value (block 434, YES), the method may proceed to block 438, where base may be added to the second vessel to neutralize the acidified fluid. The second pH probe associated with the second vessel may measure (block 440) a pH value associated with the second vessel, and a determination may be made as to whether the measured pH value associated with the second vessel is within an acceptable range of neutral pH values (e.g., a pH value range of 5.0-6.0). If the measured pH value associated with the second vessel is not within the acceptable range (block 442, NO), additional base may be added (block 438) to the vessel. If the measured pH value associated with the second vessel is within the acceptable range (block 442, YES), the addition of base to the second vessel may be ceased (block 444), and the neutralized viral inactivated fluid may be transferred (block 446) to a depth filter, and then transferred (block 558) to a sanitizing grade filter.

The second vessel may be filled (block 450) with an equilibration buffer having a known pH, and the pH associated with the second vessel may be measured (block 452) by the second pH probe associated with the second vessel. This measured pH value associated with the second vessel may be compared (block 454) to the known pH value of the equilibration buffer to determine whether the measured pH value associated with the second vessel is different from the known pH value of the equilibration buffer by greater than a threshold pH value (e.g., by more than 0.1 pH units). If the measured pH value associated with the second vessel is within 0.1 pH units of the known pH value of the equilibration buffer (block 454, NO), the method 400 may end or may proceed to block 412 where a new acidified fluid is added to the second vessel (after dumping the equilibration buffer from the second vessel).

If the pH probe's measured pH value associated with the second vessel is not within 0.1 pH units of the known pH value of the equilibration buffer (block 454, YES), an alert may be generated (block 456) indicating that the pH probe should be recalibrated. In some examples, the method 400 may include displaying or otherwise conveying the alert to an operator (e.g., via a user interface display) so that the operator can manually recalibrate the pH probe as needed. Moreover, in some examples, the method may include automatically recalibrating (block 458) the pH probe such that the pH probe measures a pH within 0.1 pH units of the equilibration buffer.

Fluids known or suspected to contain at least one enveloped virus include harvested host cell culture fluid, fluid from an effluent stream, eluate, pool, storage or hold from a unit operation comprising a harvest step, a filtration step, or a chromatography step. The fluid may be from an eluate collected from depth filtration, microfiltration, affinity chromatography, ion exchange chromatography, multimodal chromatography, hydrophobic interaction chromatography or hydroxyapatite chromatography. The fluid may be from a pool containing harvested cell culture fluid, eluate from depth filtration, eluate from microfiltration, eluate from affinity chromatography, eluate from ion exchange chromatography, eluate from multimodal chromatography, eluate from hydrophobic interaction chromatography, or eluate from hydroxyapatite chromatography. The fluid added to the first tank may be added as a single volume or may be split into portions and processed over multiple viral inactivation/neutralization cycles. The fluid may be added neat or diluted with appropriate buffers or water to achieve desired parameters or volumes. The fluid in the first tank may be a pool containing multiple eluate pools.

The pool that is added to the first tank may be diluted in a suitable medium, such as water. In one embodiment, the pool is diluted 50 to 200%. In one embodiment the pool is diluted 50 to 100%. In one embodiment the pool is diluted 50 to 75%. In one embodiment, the pool is diluted 75 to 200%. In one embodiment, the pool is diluted 75 to 100%. In one embodiment, the pool is diluted 100 to 200%.

The temperature of the fluid may range from 5-25° C. The acidification may be performed at temperatures from 5-25° C. In one embodiment, the temperature is 15-25° C. In one embodiment, the temperature is 15-20° C., in one embodiment, the temperature is 20-25° C. In one embodiment, the temperature is 20° C.

In an embodiment, the fluid is added to the first tank at a flow rate of 0.025-0.25 kg/min.

At a minimum working volume, the pH probes and the agitator must be completely immersed in the fluid, and the acid/base inlet port must be below the fluid level. In an embodiment, the working volume is from 1 to 9 liters.

Acid is added to the fluid and mixed by agitation, to acidify the fluid. The fluid may be agitated at 10-30 rpm, in one embodiment 15-30 rpm. The agitation rate should be appropriate for the fluid level and not cause splashing or vortex formation.

Suitable acids for use include formic, acidic, citric, and phosphoric at concentrations suitable to ensure viral inactivation. In one embodiment, the acidic acid is added at a concentration of approximately 70 mL/L.

The acidified fluid may remain in the first tank for a time until the fluid is sufficiently acidified, or up to the entire time needed to achieve the required degree of viral inactivation, before being transferred to the second vessel. The time for sufficient acidification is ≤30 minutes, or longer. The time for viral inactivation may be from 30 minutes to 24 hours or more.

The pH for viral inactivation is from pH 2 to 4. In one embodiment the viral inactivation pH is from 3 to 4. In one embodiment, the viral inactivation pH is from 3.5 to 4. In one embodiment, the pH is from 3.6 to 4. In one embodiment, the viral inactivation pH is from 3.7 to 4. In one embodiment, the viral inactivation pH is from 3.5 to 3.7. In one embodiment, the viral inactivation pH is from 3.5 to 3.7. In one embodiment, the viral inactivation pH is 3.6.

The acidified (or viral inactivated) fluid is then transferred to the second tank. In an embodiment, the fluid is transferred at a rate of 0.025 to 0.25 kg/min.

The transfer from tank 1 to tank 2 may be accomplished in 15 minutes or less.

At least 1 to 10 liters of acidified (or viral inactivated) fluid is transferred from tank 1 to tank 2.

The fluid may be agitated at 10-30 rpm to mix the acid with the fluid, in one embodiment the agitation is at 15-30 rpm. The agitation rate should be appropriate for the fluid level and not cause splashing or vortex formation. The system should be capable of attaining 95% homogeneity within 3 minutes after the addition of a tracer solution to a full (maximum working volume) tank of water, with the design agitation range.

If the acidified fluid is transferred to the second tank prior to the completion of the viral inactivation, the acidified fluid is maintained at the desired pH until the desired degree of inactivation has been accomplished. A determination may be made as to whether the acidified fluid from the first vessel has been maintained at a threshold amount of time for viral inactivation, in one embodiment the time for viral inactivation is 30 minutes to 24 hours or more. In one embodiment, the time for viral inactivation is from 60 to 360 minutes. In one embodiment, the time for viral inactivation may be from 60 to 90 minutes. In one embodiment the time for the viral inactivation is 60 minutes.

Once viral inactivation is complete, base is added to the viral inactivated (VI) fluid and mixed to neutralize the fluid to a desired pH. The base is added at 1-5% of the working volume of the second tank. Suitable bases for use include Tris base at a concentration of 2M. In one embodiment, 2M Tris base is added at a concentration of approximately 55 mL/L. The amount of base added may be verified by mass to ensure an additional accuracy tolerance of ±2% of the added volume. The time for neutralization can be ≤30 minutes or longer.

At least one pH probe associated with the second tank measures the pH value associated with the second tank, and a determination may be made as to whether the measured pH value associated with the second tank is within an acceptable range of neutral pH values. The target pH for neutralization is from 4.5-6. In one embodiment, the target pH for neutralization is from 4.7 to 5.5. In one embodiment, the target pH for neutralization is from 4.7 to 5.3. In one embodiment, the target pH for neutralization is from 4.7 to 5.1. In one embodiment, the target pH for neutralization is from 4.9 to 5.5. In one embodiment, the target pH for neutralization is from 4.9 to 5.3. In one embodiment, the target pH for neutralization is from 4.9 to 5.1.

The neutralization may be performed at temperatures from 5-25° C. In one embodiment, the neutralization is performed at 15-25° C. In one embodiment, the neutralization is performed at 15-20° C. In one embodiment, the neutralization is performed at 20-25° C. In one embodiment, the neutralization is performed at 20° C.

The pH of the fluid is monitored during neutralization, which may take 20 minutes or less.

The fluid may be agitated at 10-30 rpm to mix the base and the viral inactivated fluid, in one embodiment the agitation is 15-30 rpm. Once neutralization is complete, the neutralized viral inactivated fluid is transferred out to the second tank and into a holding or storage tank or onto a filter or chromatography medium.

The fluid may be transferred at a flow rate of 0.025-0.25 kg/min.

Following removal of the acidified or viral inactivated fluid from the first tank (and similarly following the removal of the neutralized viral inactivated fluid from the second tank), each tank is filled with an equilibration buffer at a known pH. Suitable buffers include acetate at concentrations of 100 mM, at pH of 5.0 to keep the pH probes immersed in liquid and wetted at all times. The volume of the of equilibration buffer must be completely purged from the tank and associated outlet tubing to eliminate mixing between equilibration buffer and the fluid for viral inactivation or neutralization processing. The pH associated with the equilibration buffer in each tank may be measured by at least one of the pH probes associated with that tank. This measured pH value may be compared to the known pH value of the equilibration buffer to determine whether the measured pH value measured by the probes in the tank is different from the known pH value of the equilibration buffer by greater than a threshold pH value (e.g., by more than ±0.1 pH units).

If the pH probe's measured pH value associated with tank is not within ±0.1 pH units of the known pH value of the equilibration buffer an alert may be generated indicating that the pH probe should be recalibrated. This may take the form of displaying or otherwise conveying the alert to an operator (e.g., via a user interface display) so that the operator can manually recalibrate the pH probe as needed. In some embodiments, the method may include automatically recalibrating the pH probe such that the pH probe measures a pH within ±0.1 pH units of the equilibration buffer.

Viruses are classified as enveloped and non-enveloped viruses. Enveloped viruses have a capsid enclosed by a lipoprotein membrane or "envelope". This envelope is made up of host cell proteins and phospholipids as well as viral glycoproteins which coat the virus as it buds from its host cell. This envelope allows the virus to identify, bind, enter, and infect target host cells. However, because of this membrane, enveloped viruses are susceptible to inactivation methods, while non-enveloped viruses are more difficult to inactivate without risk to the protein being manufactured, however, they can be removed by filtration methods.

Enveloped viruses include such virus families as herpesviridae virus, poxviridae virus, hepadnaviridae virus, flaviviridae virus, togaviridae virus, coronaviridae virus, orthomyxoviridae virus, deltavirus virus, paramyxoviridae virus, rhabdoviridae virus, bunyaviridae virus, filoviridae virus, retroviridae virus; and such viruses as human immunodeficiency virus, sindbis virus, herpes simplex virus, pseudorabies virus, sendai virus, vesicular stomatitis 5 virus, West Nile virus, bovine viral diarrhea virus, a corona virus, equine arthritis virus, severe acute respiratory syndrome virus, Moloney murine leukemia virus, and vaccinia virus.

To ensure patient safety, viral inactivation is a necessary component of the purification process when manufacturing protein therapeutics. Various methods can be employed for viral inactivation and include heat inactivation/pasteurization, UV and gamma ray irradiation, use of high intensity broad spectrum white light, addition of chemical inactivating agents, surfactants, solvent/detergent treatments, and low pH inactivation. Exposure of enveloped viruses to low pH conditions causes denaturation of the virus.

Polypeptides and proteins of interest can be of scientific or commercial interest, including protein-based therapeutics. Proteins of interest include, among other things, secreted proteins, non-secreted proteins, intracellular proteins or membrane-bound proteins. Polypeptides and proteins of interest can be produced by recombinant animal cell lines using cell culture methods and may be referred to as "recombinant proteins". The expressed protein(s) may be produced intracellularly or secreted into the culture medium from which it can be recovered and/or collected. The term "isolated protein" or "isolated recombinant protein" refers to a polypeptide or protein of interest, that is purified away from proteins or polypeptides or other contaminants that would interfere with its therapeutic, diagnostic, prophylactic, research or other use. Proteins of interest include proteins that exert a therapeutic effect by binding a target, particularly a target among those listed below, including targets derived therefrom, targets related thereto, and modifications thereof.

Proteins of interest include proteins or polypeptides that comprise an antigen-binding region or antigen-binding portion that has affinity for another molecule to which it binds (antigen), "antigen-binding proteins". Proteins of interest include antibodies, peptibodies, antibody fragments, antibody derivatives, antibody analogs, fusion proteins, genetically engineered cell surface receptors such as T cell receptors (TCRs) and chimeric antigen receptors (CARs or CAR-T cells, TRUCKs (chimeric antigen receptors that redirect T cells for universal cytokine-mediated killing), and armored CARs (designed to modulate an immunosuppressive environment)) and as well as other proteins comprising an antigen binding molecule that interacts with that targeted antigen. Also included are multispecific proteins and antibodies, including bispecific proteins and antibodies which include proteins that are recombinantly engineered to simultaneously bind and neutralize at least two different antigens or at least two different epitopes on the same antigen, which includes all of the formats for bispecific proteins and antibodies which include, but are not limited to, quadromas, knobs-in-holes, cross-Mabs, dual variable domains IgG (DVD-IgG), IgG-single chain Fv (scFv), scFv-CH3 KIH, dual action Fab (DAF), half-molecule exchange, KA-bodies, tandem scFv, scFv-Fc, diabodies, single chain diabodies (scDiabodies), scDiabodies-CH3, triple body, miniantibody, minibody, TriBi minibody, tandem diabodies, scDiabody-HAS, Tandem scFv-toxin, dual-affinity retargeting molecules (DARTs), nanobody, nanobody-HSA, dock and lock (DNL), strand exchange engineered domain SEEDbody, Triomab, leucine zipper (LUZ-Y), XmAb®; Fab-arm exchange, DutaMab, DT-IgG, charged pair, Fcab, orthogonal Fab, IgG(H)-scFv, scFV-(H)IgG, IgG(L)-scFV, IgG (L1H1)-Fv, IgG(H)-V, V(H)—IgG, IgG(L)-VV(L)-IgG, KIH IgG-scFab, 2scFV-IgG, IgG-2scFv, scFv4-Ig, Zybody, DVI-Ig4 (four-in-one), Fab-scFv, scFv-CH-CL-scFV, F(ab') 2-scFv2, scFv-KIH, Fab-scFv-Fc, tetravalent HCAb, scDiabody-Fc, diabody-Fc, intrabody, ImmTAC, HSABody, IgG-IgG, Cov-X-Body, scFv1-PEG-scFv2, single chain bispecific antibody constructs, single chain bispecific T cell engagers (BITE®), bi-specific T cell engagers, half-life extended bispecific T cell engagers (HLE BITE®s), and Heterolg BITE®s.

Also included are human, humanized, and other antigen-binding proteins, such as human and humanized antibodies, that do not engender significantly deleterious immune responses when administered to a human.

Also included are modified proteins, such as are proteins modified chemically by a non-covalent bond, covalent bond, or both a covalent and non-covalent bond. Also included are proteins further comprising one or more post-translational modifications which may be made by cellular modification systems or modifications introduced ex vivo by enzymatic and/or chemical methods or introduced in other ways.

In some embodiments, proteins of interest may include colony stimulating factors, such as granulocyte colony-stimulating factor (G-CSF). Such G-CSF agents include, but are not limited to, Neupogen® (filgrastim) and Neulasta® (pegfilgrastim). Also included are erythropoiesis stimulating agents (ESA), such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, epoetin omega, epoetin iota, tissue plasminogen activator, GLP-1 receptor agonists, as well as variants or analogs thereof and biosimilars of any of the foregoing.

In another embodiment, proteins of interest include abciximab, adalimumab, adecatumumab, aflibercept, alemtuzumab, alirocumab, anakinra, atacicept, axicabtagene ciloleucel, basiliximab, belimumab, bevacizumab, biosozumab, blinatumomab, brentuximab vedotin, brodalumab, cantuzumab mertansine, canakinumab, catumaxomab, cetuximab, certolizumab pegol, conatumumab, daclizumab, denosumab, eculizumab, edrecolomab, efalizumab, epratuzumab, erenumab, ertumaxomab, etanercept, evolocumab, floteuzmab (MGD006), galiximab, ganitumab, lutikizumab (ABT981), gemtuzumab, golimumab, ibritumomab tiuxetan, infliximab, ipilimumab, lerdelimumab, lumiliximab, lxdkizumab, lymphomun (FBTA05), mapatumumab, motesanib diphosphate, muromonab-CD3, natalizumab, nesiritide, nimotuzumab, nivolumab, ocrelizumab, ofatumumab, omalizumab, oprelvekin, ozoralixumab (ATN103), palivizumab, panitumumab, pasotuxizumab (AMG112, MT112), pembrolizumab, pertuzumab, pexelizumab, ranibizumab, remtolumab (ABT122), rilotumumab, rituximab, romiplostim, romosozumab, sargamostim, sclerostin, solitomab, targomiRs, tezepelumab, tisagenlecleucel, tocilizumab, tositumomab, trastuzumab, ustekinumab, vanucizumab (RG7221), vedolizumab, visilizumab, volociximab, zanolimumab, zalutumumab, AMG211 (MT111, Medi-1565), AMG330, AMG420 (B1836909), AMG-110 (MT110), MDX-447, TF2, rM28, HER2Bi-aATC, GD2Bi-aATC, MGD006, MGD007, MGD009, MGD010, MGD011 (JNJ64052781), IMCgp100, indium-labeled IMP-205, xm734, LY3164530, OMP-305BB3, REGN1979, COV322, ABT112, ABT165, RG-6013 (ACE910), RG7597 (MEDH7945A), RG7802, RG7813(R06895882), RG7386, BITS7201A (RG7990), RG7716, BFKF8488A (RG7992), MCLA-128, MM-111, MM141, MOR209/ES414, MSB0010841, ALX-0061, ALX0761, ALX0141; B11034020, AFM13, AFM11, SAR156597, FBTA05, PF06671008, GSK2434735, MEDI3902, MEDI0700, MEDI735, as well as variants or analogs thereof and biosimilars of any of the foregoing.

In some embodiments, proteins of interest may include proteins that bind specifically, alone or in combination, to one or more CD proteins, HER receptor family proteins, cell adhesion molecules, growth factors, nerve growth factors, fibroblast growth factors, transforming growth factors (TGF), insulin-like growth factors, osteoinductive factors, insulin and insulin-related proteins, coagulation and coagulation-related proteins, colony stimulating factors (CSFs), other blood and serum proteins blood group antigens; receptors, receptor-associated proteins, growth hormones, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins.

In some embodiments proteins of interest bind to one of more of the following, alone or in any combination: CD proteins including but not limited to CD2, CD3 (alpha, beta, delta, epsilon, gamma, zeta), CD4, CD5, CD7, CD8, CD8alpha, CD16, CD19, CD20, CD22, CD25, CD27, CD28, CD28T, CD30, CD33, CD34, CD37, CD38, CD40, CD45, CD49a, CD64, CD70, Ig alpha (CD79a), CD80, CD86, CD123, CD133, CD134, CD137, CD138, CD154, CD171, CD174, CD247 (B7-H3). HER receptor family proteins, including, for instance, HER2, HER3, HER4, and the EGF receptor, EGFRvIII, cell adhesion molecules, for example, LFA-1, CD1 1a/CD18, Mol, p150,95, VLA-4, ICAM-1, VCAM, and alpha v/beta 3 integrin, growth factors, including but not limited to, for example, vascular endothelial growth factor ("VEGF"); VEGFR2, growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), Cripto, transforming growth factors (TGF), including, among others, TGF-α and TGF-β, including TGF-β1, TGF-β2, TGF-β3, TGF-β4, or TGF-β5, insulin-like growth factors-I and -II (IGF-I and IGF-II), des(1-3)-IGF-I (brain IGF-I), and osteoinductive factors, insulins and insulin-related proteins, including but not limited to insulin, insulin A-chain, insulin B-chain, proinsulin, and insulin-like growth factor binding proteins; (coagulation and coagulation-related proteins, such as, among others, factor VIII, tissue factor, von Willebrand factor, protein C, alpha-1-antitrypsin, plasminogen activators, such as urokinase and tissue plasminogen activator ("t-PA"), bombazine, thrombin, thrombopoietin, and thrombopoietin receptor, colony stimulating factors (CSFs), including the following, among others, M-CSF, GM-CSF, and G-CSF, other blood and serum proteins, including but not limited to albumin, IgE, and blood group antigens, receptors and receptor-associated proteins, including, for example, flk2/flt3 receptor, obesity (OB) receptor, growth hormone receptors, and T-cell receptors; neurotrophic factors, including but not limited to, bone-derived neurotrophic factor (BDNF) and neurotrophin-3, -4, -5, or -6 (NT-3, NT-4, NT-5, or NT-6); relaxin A-chain, relaxin B-chain, and prorelaxin, interferons, including for example, interferon-alpha, -beta, and -gamma, interleukins (ILs), e.g., IL-1 to IL-10, IL-12, IL-15, IL-17, IL-23, IL-12/IL-23, IL-2Ra, IL-2Rbeta, IL-2R gamma, IL-7R alpha, IL1-R1, IL-6 receptor, IL-4 receptor and/or IL-13 to the receptor, IL-13RA2, or IL-17 receptor, IL-1RAP, viral antigens, including but not limited to, an AIDS envelope viral antigen, lipoproteins, calcitonin, glucagon, atrial natriuretic factor, lung surfactant, tumor necrosis factor-alpha and -beta, enkephalinase, BCMA, IgKappa, ROR-1, ERBB2, mesothelin, RANTES (regulated on activation normally T-cell expressed and secreted), mouse gonadotropin-associated peptide, Dnase, FR-alpha, inhibin, and activin, integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, MIC (MIC-a, MIC-B), ULBP 1-6, EPCAM, addressins, regulatory proteins, immunoadhesins, antigen-binding proteins, somatropin, CTGF, CTLA4, eotaxin-1, MUC1, CEA, c-MET, Claudin-18, GPC-3, EPHA2, FPA, LMP1, MG7, NY-ESO-1, PSCA, ganglioside GD2, glanglioside GM2, BAFF, BAFFR, OPGL (RANKL), myostatin, Dickkopf-1 (DKK-1), Ang2, NGF, IGF-1 receptor, hepatocyte growth factor (HGF), TRAIL-R2, c-Kit, B7RP-1, PSMA, NKG2D-1, programmed cell death protein 1 and ligand, PD1 and PDL1, mannose receptor/hCG3, hepatitis-C virus, mesothelin dsFv[PE38 conjugate, *Legionella pneumophila* (lly), IFN gamma, interferon gamma induced protein 10 (IP10), IFNAR, TALL-1, TNFα, TNFr, TL1A, thymic stromal lymphopoietin (TSLP), proprotein convertase subtilisin/Kexin Type 9 (PCSK9), stem cell factors, Flt-3, calcitonin gene-related peptide (CGRP), OX40L, α4β7, platelet specific (platelet glycoprotein IIb/IIIb (PAC-1), transforming growth factor beta (TFG3), STEAP1, Zona pellucida sperm-binding protein 3 (ZP-3), TWEAK, platelet derived growth factor receptor alpha (PDGFRa), 4-1BB/CD137, ICOS, LIGHT (tumor necrosis factor superfamily member 14; TMFSF14), DAP-10, Fc gamma receptor, MHC class I molecule, signaling lymphocytic activation molecule, BTLA, Toll ligand receptor, CDS, GITR, HVEM (LIGHT R), KIRDS, SLAMF7, NKp80 (KLRF1), NKp44, NKp30, NKp46, ITGA4, VLA1, VLA-6, IA4, CD49D, ITGA6, CD49f, ITGAD, CDI-Id, ITGAE, CD103, ITGAL, CDI-Ia, LFA-1, ITGAM, CDI-Ib, ITGAX, CDI-Ic, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, 41-BB, GADS, SLP-76, PAG/Cbp, CD19a, CD83 ligand, 5T4, AFP, ADAM 17, 17-A, ART-4, $\alpha_v\beta_6$ integrin, BAGE. Bcr-abl, BCMA, B7-H3, B7-H6, CAIX, CAMEL, CAP-1, Carbonic anhydrase IX, CASP-8, CDC27m, CD19, CD20, CD22, CD30, CD33, CD44, CD44v6, CD44v7/8, CD70 (CD27L or TNFSF7), CD79a, CD79b, CD123, CD138, CD171, CDK4/m, cadherin 19 (CDH19), Placental-Cadherin (CDH3), CEA, CLL-1, CSPG4, CT, Cyp-B, DAM, DDL3, EBV, EGFR, EGFRvIII, EGP2, EGP40, ELF2M, ErbB2 (HER2), EPCAM, EphA2, EpCAM, ETV6-AML1, FAP, fetal AchR, FLT3, FRa, G250, GAGE, GD2, GD3, 'Glypican-3 (GPC3), GNT-V, GP-100, HAGE, HBV, HCV, HER-2/neu, HLA-A, HPV, HSP70, HST-2, hTERT, iCE, IgE, IL-11Ra, IL-13Ra2, Kappa, KIAA0205, LAGE, Lambda, LDLR/FUT, Lewis-Y, MAGE, MAGE1, MAGEB2, MART-1, /Melan-A, MC1R, MCSP, MUM-1, MUM-2, MUM-3, mesothelin (MSLN), Muc1, Muc16, Myosin/m, NA88-A, NCAM, NKG2D Ligands, NY-ESO-1, P15, p190 minorbcr-abl, PML/RARa, PRAME, PSA, PSCA, PSMA, RAGE, ROR1, RU1, RU2, SAGE, SART, SSX-1, SSX-2, SSX-3, Survivin, TAA, TAG72, TEL/AML1, TEMs, TPI, TRP-1, TRP-2, TRP-2/INT2, VEGFR2, WT1, and biologically active fragments or variants of any of the foregoing.

Proteins of interest according to the invention encompass all of the foregoing and further include antibodies comprising 1, 2, 3, 4, 5, or 6 of the complementarity determining regions (CDRs) of any of the aforementioned antibodies. Also included are variants that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a protein of interest. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

By "culture" or "culturing" is meant the growth and propagation of cells outside of a multicellular organism or tissue. Suitable culture conditions for host cells, such as mammalian cells, are known in the art. Cell culture media and tissue culture media are interchangeably used to refer to media suitable for growth of a host cell during in vitro cell culture. Typically, cell culture media contains a buffer, salts, energy source, amino acids, vitamins and trace essential elements. Any media capable of supporting growth of the appropriate host cell in culture can be used and may be further supplemented with other components to maximize cell growth, cell viability, and/or recombinant protein production in a particular cultured host cell, are commercially available. Various media formulations can be used during the life of the cell culture. Host cells may be cultured in suspension or in an adherent form, attached to a solid substrate. Cell cultures can be established in fluidized bed bioreactors, hollow fiber bioreactors, roller bottles, shake flasks, or stirred tank bioreactors, with or without microcarriers Cell cultures can be operated in a batch, fed batch, continuous, semi-continuous, or perfusion mode. Mammalian host cell lines, such as CHO cells, can be cultured in bioreactors at a smaller scale of less than 100 ml to less than 1000 mls. Alternatively, larger scale bioreactors that contain 1000 mls to over 20,000 liters of media can be used. Large scale cell cultures, such as for clinical and/or commercial scale biomanufacturing of protein therapeutics, may be maintained for weeks and even months, while the cells produce the desired protein(s).

The cell culture fluid containing the expressed recombinant protein can then be harvested from the cell culture in the bioreactor. Methods for harvesting protein expressed from suspension cells are known in the art and include, but are not limited to, acid precipitation, accelerated sedimentation such as flocculation, separation using gravity, centrifugation, acoustic wave separation, filtration including membrane filtration using ultrafilters, microfilters, tangential flow filters, depth, and alluvial filtration filters. Recombinant proteins expressed by prokaryotes may be retrieved from inclusion bodies in the cytoplasm by redox folding processes known in the art.

The recombinant protein of interest in the clarified harvested cell culture fluid can then be purified, or partially purified, away from any remaining impurities, such as remaining cell culture media, cell extracts, undesired components, host cell proteins, improperly expressed proteins, contaminants, microorganisms such as bacteria and viruses, aggregates, and the like, using one or more unit operations.

The term "unit operation" refers to a functional step that is performed in a process for purifying a recombinant protein, such as from a liquid culture medium. For example, a unit of operation can include steps such as, but not limited to, harvesting, capturing, purifying, polishing, viral inactivation, virus filtering, and/or adjusting the concentration and formulation of fluids containing the recombinant protein of interest. Unit operations can also include steps where fluid is pooled, held, and/or stored, such as capture pools, following harvest, chromatography, viral inactivation and neutralization, or filtration, where the fluid placed in holding or storing vessels. A single unit operation may be designed to accomplish multiple objectives in the same operation, such as harvest and viral inactivation or capture and viral inactivation.

A capture unit operation includes capture chromatography that makes use of resins and/or membranes containing agents that will bind and/or interact with the recombinant protein of interest, for example affinity chromatography, size exclusion chromatography, ion exchange chromatography, hydrophobic interaction chromatography (HIC), immobilized metal affinity chromatography (IMAC), and the like. Such materials are known in the art and are commercially available. Affinity chromatography may include, for example, a substrate-binding capture mechanism, an antibody- or antibody fragment-binding capture mechanism, an aptamer-binding capture mechanism, and a cofactor-binding capture mechanism, for example. Exemplary affinity chromatography media includes Protein A, Protein G, Protein A/G, and Protein L. The recombinant protein of interest can be tagged with a polyhistidine tag and subsequently purified from IMAC using imidazole or an epitope, such a FLAG® protein tag and subsequently purified by using a specific antibody directed to such epitope.

The inactivation of enveloped viruses known or suspected to be contained in a fluid can be done at any time during the downstream process. During biological drug substance manufacturing, inactivation of virus in a fluid comprising a recombinant protein of interest can take place in one or more independent viral inactivation unit operations. In one embodiment viral inactivation takes place prior to, as part of, or following a harvest unit operation. In one embodiment viral inactivation takes place following a harvest unit operation, in a related embodiment the harvest unit operation included ultrafiltration and/or microfiltration. In one embodiment, viral inactivation takes place prior to, as part of, or following a chromatography unit operation. In one embodiment, viral inactivation takes place prior to, as part of, or following one or more capture chromatography unit operations. In one embodiment, viral inactivation takes place prior to, as part of, or following one or more affinity chromatography unit operations. In one embodiment, viral inactivation takes place prior to, as part of, or following one or more of Protein A chromatography, Protein G chromatography, Protein A/G chromatography, Protein L chromatography, and/or IMAC chromatography. In one embodiment, viral inactivation takes place prior to, as part of, or following one or more polish chromatography unit operations. In one embodiment, viral inactivation takes place prior to, as part of, or following one or more ion exchange chromatography, hydrophobic interaction chromatography; mixed modal or multimodal chromatography, and/or hydroxyapatite chromatography unit operations. In one embodiment, viral inactivation takes place prior to, as part of, or following one or more ion exchange chromatography. In one embodiment, viral inactivation takes place prior to, as part of, or following a cation exchange chromatography unit operation. In one embodiment, viral inactivation takes place prior to, as part of, or following an anion exchange chromatography unit operation. In one embodiment, viral inactivation takes place prior to, as part of, or following a multimodal or mixed modal chromatography unit operation. In one embodiment, viral inactivation takes place prior to, as part of, or following a hydrophobic interaction chromatography unit operation. In one embodiment, viral inactivation takes place prior to, as part of, or following a hydroxyapatite chromatography unit operation. In one embodiment, viral inactivation takes place prior to, as part of, or following one or more ion exchange chromatography, hydrophobic interaction chromatography; mixed modal or multimodal chromatography, and/or hydroxyapatite chromatography unit operations. In one embodiment, viral inactivation takes place prior to, as part of, or following a filter unit operation. In one embodiment, viral inactivation takes place prior to, as part of, or following a virus filtration unit operation. In one embodiment, viral inactivation takes place prior to, as part of, or following a depth filtration unit operation. In one embodiment, viral inactivation takes place prior to, as part of, or following a sterile filtration unit operation. In one embodiment, viral inactivation takes place prior to, as part of, or following one or more of a depth filtration unit operation and/or a sterile filtration unit operation. In one embodiment, viral inactivation takes place and/or prior to or following one or more ultrafiltration/diafiltration unit operations.

A viral inactivation unit operation may be followed by a filtration and/or chromatography unit operation. In one embodiment, viral inactivation takes place prior to, as part of, or following depth filtration and/or sterile filtration unit operation, to remove inactivated viruses, other inactivating agents such as surfactants and detergents, turbidity and/or precipitation.

The term "polishing" is used herein to refer to one or more chromatographic steps performed to remove remaining contaminants and impurities such as DNA, host cell proteins; product-specific impurities, variant products and aggregates and virus adsorption from a fluid including a recombinant protein that is close to a final desired purity. For example, polishing can be performed in bind and elute mode by passing a fluid including the recombinant protein through a chromatographic column(s) or membrane absorber(s) that selectively binds to either the target recombinant protein or the contaminants or impurities present in a fluid including a recombinant protein. In such an example, the eluate/filtrate of the chromatographic column(s) or membrane absorber(s) includes the recombinant protein.

The polish chromatography unit operation makes use chromatography resins and/or membranes containing agents that can be used in a flow-through mode, an overloaded or frontal chromatography mode, or bind and elute mode, for example. Chromatography media suitable for use in in such operations include ion exchange chromatography (IEX), such as anion exchange chromatography (AEX) and cation exchange chromatography (CEX); hydrophobic interaction chromatography (HIC); mixed modal or multimodal chromatography (MM), hydroxyapatite chromatography (HA); reverse phase chromatography and gel filtration.

Provided are methods for inactivating enveloped viruses during purification of a recombinant protein of interest comprising, comprising obtaining a fluid known or suspected to contain at least one enveloped virus; subjecting the fluid to the systems or methods described herein at a concentration and for a time sufficient to cause viral inactivation followed by neutralization of the viral inactivated fluid. The neutralized viral inactivated fluid can be stored for later use. The neutralized viral inactivated fluid can be subjected to at least one unit operation which includes at least a filtration step or a chromatography step.

Also provided are methods for inactivating enveloped viruses during purification of a recombinant protein of interest comprising, comprising obtaining a fluid known or suspected to contain at least one enveloped virus; subjecting the fluid to the systems or methods described herein at a concentration and for a time sufficient to cause viral inactivation; and subjecting the neutralized viral inactivated fluid to at least one unit operation which includes at least a filtration step or a chromatography step. In one embodiment the filter step comprises depth filtration. In one embodiment, the filtration step comprises depth filtration and sterile filtration. In one embodiment the chromatography step comprises affinity chromatography. In one embodiment the affinity chromatography is selected from Protein A chromatography, Protein G chromatography, Protein A/G chromatography, Protein L chromatography, or IMAC. In one embodiment the chromatography step comprises one or more polish chromatography steps. In one embodiment the polish chromatography is selected from ion exchange chromatography, hydrophobic interaction chromatography, multimodal or mixed-modal chromatography, or hydroxyapatite chromatography.

Also provided are methods for producing an isolated, purified, recombinant protein of interest comprising establishing a cell culture in a bioreactor with a host cell expressing a recombinant protein and culturing the cells to express the recombinant protein of interest; harvesting cell culture fluid containing the recombinant protein of interest; processing the fluid containing the recombinant protein of interest through at least two unit operations, wherein at least one unit operation comprises a viral inactivation system or method described herein for a time sufficient to cause inactivation and neutralization of enveloped virus; processing the neutralized viral inactivated fluid containing the recombinant protein of interest through at least one additional unit operation; and obtaining an isolated, purified, recombinant protein of interest.

Also provides are isolated, purified, recombinant proteins of interest made using the systems and methods described herein. Also provided are pharmaceutical compositions comprising isolated proteins of interest made using the systems and methods described herein.

Although the preceding text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Throughout this specification, unless indicated otherwise, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may likewise be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Hardware modules can provide information to, and receive information from, other hardware modules. Accordingly, the described hardware modules may be regarded as being communicatively coupled. Where multiple such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, in some embodiments, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" or "in some embodiments" in various places in the specification are not necessarily all referring to the same embodiment or embodiments.

Some embodiments may be described using the terms "coupled," "connected," "communicatively connected," or "communicatively coupled," along with their derivatives. These terms may refer to a direct physical connection or to an indirect (physical or communication) connection. For example, some embodiments may be described using the term "coupled" to indicate that two or more elements are in direct physical or electrical contact. The term "coupled," however, may also mean that two or more elements are not in direct contact with each other, but yet still co-operate or interact with each other. Unless expressly stated or required by the context of their use, the embodiments are not limited to direct connection.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the words "a" or "an" are employed to describe elements and components of the embodiments herein. This is done merely for convenience and to give a general sense of the description. This description, and the claims that follow, should be read to include one or at least one, and the singular also includes the plural unless the context clearly indicates otherwise.

Upon reading this disclosure, those of skill in the art will appreciate still additional alternative structural and functional designs for automated cycles of pH adjustment. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

Finally, the patent claims at the end of this patent application are not intended to be construed under 35 U.S.C. § 112(f), unless traditional means-plus-function language is expressly recited, such as "means for" or "step for" language being explicitly recited in the claims.

What is claimed is:

1. An automated system for low pH viral inactivation, wherein the pH is from 2 to 4, comprising:

a first vessel;

a second vessel;

a first pH probe associated with the first vessel and configured to measure the pH of contents of the first vessel;

a source of a fluid known or suspected to contain at least one enveloped virus to be transferred to the first vessel;

an acid pump configured to pump acid into the first vessel after the fluid is transferred into the first vessel to form an acidified pool and configured to cease pumping acid into the first vessel responsive to the first pH probe measuring a first pH value that is within a tolerance band of a target pH value for viral inactivation;

a transfer pump configured to pump the acidified pool from the first vessel to the second vessel responsive to the first pH probe measuring the first pH value that is below the target pH value for viral inactivation, and responsive to the acid pump ceasing to pump acid into the first vessel;

a first buffer pump configured to pump a first equilibration buffer, having a first known pH value, into the first vessel responsive to the entire acidified pool being pumped out of the first vessel; and an alert generator configured to:

compare a second pH value, measured by the first pH probe after the first equilibration buffer is pumped into the first vessel, to the first known pH value of the first equilibration buffer;

determine whether the second pH value measured by the first pH probe is different from the first known pH value of the first equilibration buffer by greater than a threshold pH value; and generate a first alert responsive to the second pH value measured by the first pH probe being different from the first known pH of the first equilibration buffer by greater than the threshold pH value.

2. The automated system for low pH viral inactivation of claim 1, further comprising a source pump configured to pump the fluid into the first vessel from the source based at least in part on a signal indicating that the first vessel is empty.

3. The automated system for low pH viral inactivation of claim 1, wherein the first buffer pump is configured to pump the first equilibration buffer into the first vessel based at least in part on a signal indicating that the first vessel is empty.

4. The automated system for low pH viral inactivation of claim 1, further comprising:

a second pH probe associated with the second vessel and configured to measure the pH of contents of the second vessel;

a base pump configured to pump base into the second vessel responsive to an elapsed time, from the entire acidified pool being pumped into the second vessel, exceeding a threshold amount of time for reducing a concentration of virus in the acidified pool to a predetermined safe level, and configured to cease pumping base into the second vessel responsive to the second pH probe measuring a first pH value that is within a threshold range of neutral pH values, wherein the base neutralizes the acidified pool to form a neutralized viral inactivated pool;

a discharge pump configured to pump the neutralized viral inactivated pool from the second vessel into a filter for treatment of the neutralized viral inactivated pool;

a second buffer pump configured to pump a second equilibration buffer, having a second known pH value, into the second vessel responsive to the entire neutralized viral inactivated pool being pumped out of the second vessel; and wherein the alert generator is further configured to:

compare a second pH value, measured by the second pH probe after the second equilibration buffer is pumped into the second vessel, to the second known pH value of the second equilibration buffer;

determine whether the second pH value measured by the second pH probe is different from the second known pH value of the second equilibration buffer by greater than a threshold pH value; and generate a second alert responsive to the second pH value measured by the second pH probe being different from the second known pH of the second equilibration buffer by greater than the threshold pH value.

5. The automated system for low pH viral inactivation of claim 4, wherein the first equilibration buffer and the second equilibration buffer are the same equilibration buffer.

6. The automated system for low pH viral inactivation of claim 4, wherein the first equilibration buffer and the second equilibration buffer are distinct equilibration buffers.

7. The automated system for low pH viral inactivation of claim 4, wherein the transfer pump is configured to pump the acidified pool from the first vessel to the second vessel based at least in part on a signal indicating that the second vessel is empty.

8. The automated system for low pH viral inactivation of claim 4, wherein the second buffer pump is configured to pump the second equilibration buffer into the second vessel based at least in part on a signal indicating that the second vessel is empty.

9. The automated system for low pH viral inactivation of claim 4, further comprising:

a third vessel; and a collection pump configured to pump the filtered pool from the filter to the third vessel.

10. The automated system for low pH viral inactivation of claim 9, wherein the collection pump is configured to pump the filtered pool from the second vessel to the third vessel based at least in part on a signal indicating that the third vessel is empty.

11. The automated system for low pH viral inactivation of claim 4, further comprising one or more additional pH probes associated with the second vessel and configured to measure the pH of contents of the second vessel.

12. The automated system for low pH viral inactivation of claim 4, further comprising:

a second pH probe recalibrator configured to automatically recalibrate the second pH probe responsive to the second alert.

13. The automated system for low pH viral inactivation of claim 4, further comprising:

an operator display configured to display one or more of the first alert or the second alert to an operator associated with the system.

14. The automated system of low pH viral inactivation of claim 4, further comprising a holding vessel, wherein the neutralized viral inactivated pool from the second vessel is transferred to the holding vessel.

15. The automated system of low pH viral inactivation of claim 4, further comprising a depth filter, wherein the neutralized viral inactivated pool from the second vessel is transferred to the depth filter configured to perform depth filtration to form a neutralized viral inactivated eluate.

16. The automated system of low pH viral inactivation of claim 15, further comprising a sterile filter, wherein following depth filtration, the neutralized viral inactivated eluate is transferred to the sterile filter.

17. The automated system of low pH viral inactivation of claim 4, further comprising a first polish chromatography column, wherein the neutralized viral inactivated pool from the second vessel is transferred to the first polish chromatography column.

18. The automated system for low pH viral inactivation of claim 1, further comprising:

a first pH probe recalibrator configured to automatically recalibrate the first pH probe responsive to the first alert.

19. The automated system for low pH viral inactivation of claim 1, further comprising one or more additional pH probes associated with the first vessel and configured to measure the pH of contents of the first vessel.

20. An automated method of low pH viral inactivation, wherein the pH is from 2 to 4, the method comprising:

adding a pool comprising fluid known or suspected to contain at least one enveloped virus to a first vessel;

adding acid to the first vessel;

measuring, by a first pH probe associated with the first vessel, a first pH value associated with the first vessel;

ceasing, based on the first measured pH value associated with the first vessel being within a tolerance band of a target pH value for viral inactivation, the addition of acid to the first vessel;

transferring the pool from the first vessel to a second vessel;

filling the first vessel with an equilibration buffer having a known pH value;

measuring, by the first pH probe, a second pH value associated with the first vessel;

comparing the second measured pH value associated with the first vessel to the known pH value of the equilibration buffer;

determining whether the second measured pH value associated with the first vessel is different from the known pH value of the equilibration buffer by greater than a threshold pH value; and generating a first alert responsive to the second measured pH value associated with the first vessel being different from the known pH value of the equilibration buffer by greater than the threshold pH value.

* * * * *